United States Patent
Desai et al.

(10) Patent No.: US 12,053,561 B2
(45) Date of Patent: Aug. 6, 2024

(54) CLICK-CROSSLINKED HYDROGELS AND METHODS OF USE

(71) Applicant: President and Fellows of Harvard College, Cambridge, MA (US)

(72) Inventors: Rajiv Desai, San Diego, CA (US); Neel Satish Joshi, Somerville, MA (US); David J. Mooney, Sudbury, MA (US); Sandeep T. Koshy, Boston, MA (US); Alexander Stafford, Revere, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 17/022,062

(22) Filed: Sep. 15, 2020

(65) Prior Publication Data

US 2021/0128790 A1    May 6, 2021

Related U.S. Application Data

(63) Continuation of application No. 15/301,466, filed as application No. PCT/US2015/024523 on Apr. 6, 2015, now Pat. No. 10,821,208.

(60) Provisional application No. 61/975,375, filed on Apr. 4, 2014.

(51) Int. Cl.
| | |
|---|---|
| A61L 27/52 | (2006.01) |
| A61L 27/20 | (2006.01) |
| A61L 27/22 | (2006.01) |
| A61L 27/26 | (2006.01) |
| A61L 27/38 | (2006.01) |
| A61L 27/54 | (2006.01) |
| C07D 237/26 | (2006.01) |
| C07K 14/78 | (2006.01) |
| C08B 37/00 | (2006.01) |

(52) U.S. Cl.
CPC ............ *A61L 27/52* (2013.01); *A61L 27/20* (2013.01); *A61L 27/222* (2013.01); *A61L 27/26* (2013.01); *A61L 27/3886* (2013.01); *A61L 27/54* (2013.01); *C07D 237/26* (2013.01); *C07K 14/78* (2013.01); *C08B 37/0084* (2013.01); *A61L 2300/22* (2013.01); *A61L 2300/23* (2013.01); *A61L 2300/252* (2013.01); *A61L 2300/256* (2013.01); *A61L 2300/258* (2013.01); *A61L 2300/414* (2013.01); *A61L 2300/64* (2013.01); *A61L 2400/06* (2013.01); *A61L 2400/18* (2013.01)

(58) Field of Classification Search
CPC ........ A61L 27/52; A61L 27/20; A61L 27/222; A61L 27/26; A61L 27/54; C07D 237/26; C08L 89/00
See application file for complete search history.

(56) References Cited

U.S. PATENT DOCUMENTS

| 8,691,195 B2 * | 4/2014 | Chung ............ A61K 8/64 |
| | | 514/21.7 |
| 10,821,208 B2 | 11/2020 | Desai et al. |
| 2009/0220607 A1 | 9/2009 | Kiser et al. |
| 2009/0324720 A1 | 12/2009 | He et al. |
| 2010/0291171 A1 | 11/2010 | Crescenzi et al. |
| 2012/0156164 A1 | 6/2012 | Park et al. |
| 2013/0231474 A1 | 9/2013 | Auzely et al. |
| 2014/0024815 A1 | 1/2014 | Hult et al. |
| 2014/0058058 A1 | 2/2014 | Song et al. |
| 2014/0348772 A1 ‡ | 11/2014 | Goepferich ........ A61L 27/52 |
| | | 424/78.3 |

FOREIGN PATENT DOCUMENTS

| DE | 102011117839 A1 ‡ | 5/2013 | ............ A61L 27/52 |
| WO | 2010/099818 A1 | 9/2010 | |

OTHER PUBLICATIONS

Hellio, Dominique, and Madeleine Djabourov. "Physically and chemically crosslinked gelatin gels." Macromolecular Symposia. vol. 241. No. 1. Weinheim: Wiley-VCH Verlag, 2006. (Year: 2006).*
Nichol, Jason W., et al. "Cell-laden microengineered gelatin methacrylate hydrogels." Biomaterials 31.21 (2010): 5536-5544. (Year: 2010).*
Alge et al. Biomacromolecules 2013, 14, 4, Suporting information, pp. 1-14. (Year: 2013).*
Jiang et al., Click hydrogels, microgels and nanogels: emerging platforms for drug delivery and tissue engineering. Biomaterials Jun. 2014;35(18):4969-85.‡
Barker et al., Tetrazine-norbornene click reactions to functionalize degradable polymers derived from lactide. Macromol. Rapid Commun. Sep. 1, 2011;32(17):1362-6.‡
Lee et al., Acta Biomaterialia, 10, pp. 4167-4174. (Year: 2014).‡
Crescenzi et al., Biomacromolecules, 8, pp. 1844-1850. (Year: 2007).‡
Sanyal, Macromol. Chem. Phys. 211, 1417-1425. (Year: 2010).‡
Alge et al., Biomacromolecules, 14, pp. 949-953. (Year: 2013).‡
Kharkar et al., Chem. Soc. Rev., 42 pp. 7335-7372 (Year: 2013).‡
Lee et al., Prog Polym Sci, 37(1), pp. 106-126. (Year: 2012).‡
Matrix Scientific, MSDS for 1-Bicyclo[2.2.1]hept-5-en-2-ylmethanamine, pp. 1-3. (Year: 2010).‡
Hansell et al., J. Am. Chem. Soc., 2011, 133, 13828-13831 and S1-S20.‡
Alge et al., Synthetically tractable click hydrogels for 3D cell culture formed using tetrazine-norbornene chemistry. S1-S14 (2013).
Crescenzi et al., Novel hydrogels via click chemistry: synthesis and potential biomedical applications. Biomacromolecules. Jun. 2007;8(6):1844-50.
Hansell et al., Additive-free clicking for polymer functionalization and coupling by tetrazine-norbornene chemistry. J Am Chem Soc. Sep. 7, 2011;133(35):13828-31.

(Continued)

*Primary Examiner* — Abigail Vanhorn
(74) *Attorney, Agent, or Firm* — McCarter & English, LLP; Maria Laccotripe Zacharakis; Yelena Margolin

(57) ABSTRACT

The present disclosure provides click-crosslinked hydrogels and methods of use.

20 Claims, 9 Drawing Sheets

Specification includes a Sequence Listing.

(56) References Cited

OTHER PUBLICATIONS

Kharkar et al., Designing degradable hydrogels for orthogonal control of cell microenvironments. Chem Soc Rev. Sep. 7, 2013;42(17):7335-72.
Lee et al., Alginate: properties and biomedical applications. Prog Polym Sci. Jan. 2012;37(1):106-126.
Lee et al., The effects of varying poly(ethylene glycol) hydrogel crosslinking density and the crosslinking mechanism on protein accumulation in three-dimensional hydrogels. Acta Biomater. Oct. 2014; 10(10):4167-74.
Matrix Scientific, 1-Bicyclo[2.2.1]hept-5-en-2-ylmethanamine. Material Safety Data Sheet. Catalog No. 038023. 3 pages. Sep. 25, 2010.
Sanyal, Diels-Alder cycloaddition-cycloreversion: a powerful combo in materials design. Macromol Chem Phys. 2010;211:1417-25.
International Search Report and Written Opinion for Application No. PCT/US2015/024523, dated Jun. 25, 2015. 8 pages.

\* cited by examiner
‡ imported from a related application

Click Alginate Hydrogel

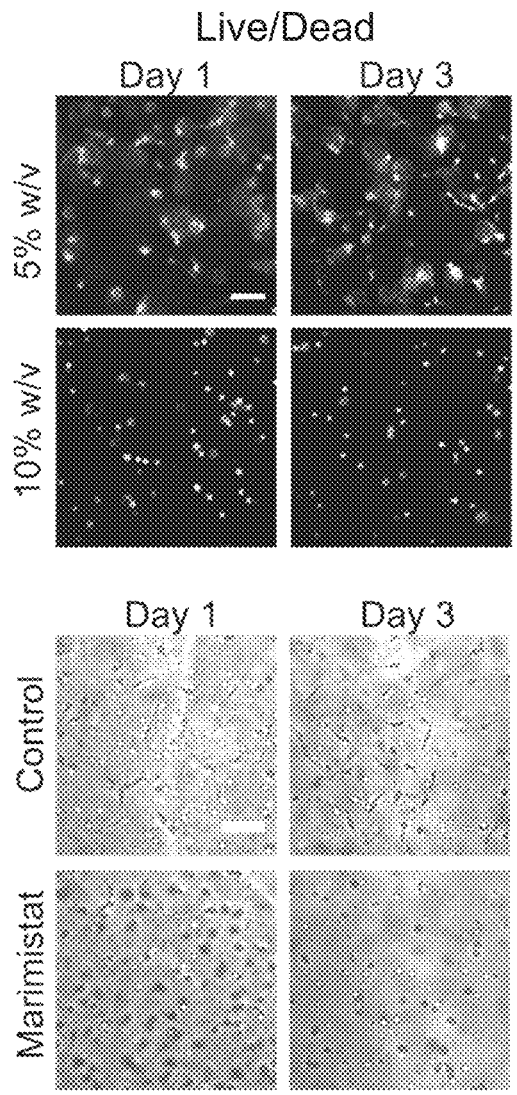
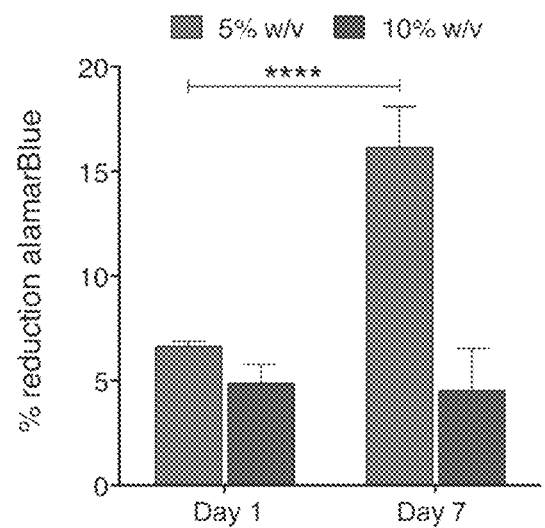
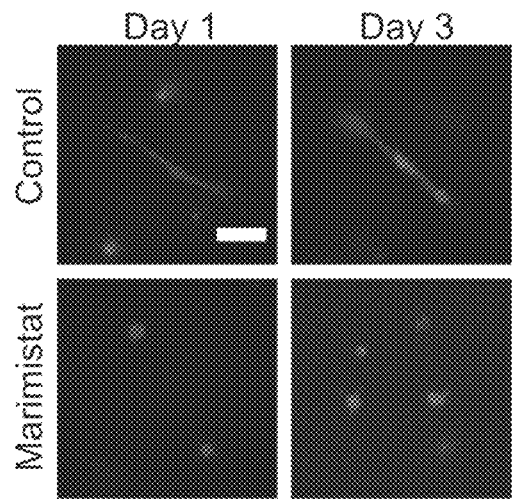

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: cell adhesive peptide

<400> SEQUENCE: 1

Arg Gly Asp Cys
1

<210> SEQ ID NO 2
<211> LENGTH: 4
<212> TYPE: PRT
<213> ORGANISM: Artificial Sequence
<220> FEATURE:
<223> OTHER INFORMATION: cell adhesive peptide

<400> SEQUENCE: 2

Arg Gly Asp Ser
1

<210> SEQ ID NO 3
<211> LENGTH: 6
<212> TYPE: PRT
<213> ORGANISM: Artificial Sequence
<220> FEATURE:
<223> OTHER INFORMATION: cell adhesive peptide

<400> SEQUENCE: 3

Lys Gln Ala Gly Asp Val
1               5

<210> SEQ ID NO 4
<211> LENGTH: 4
<212> TYPE: PRT
<213> ORGANISM: Artificial Sequence
```

```
<220> FEATURE:
<223> OTHER INFORMATION: cell adhesive peptide

<400> SEQUENCE: 4

Val Ala Pro Gly
1

<210> SEQ ID NO 5
<211> LENGTH: 10
<212> TYPE: PRT
<213> ORGANISM: Artificial Sequence
<220> FEATURE:
<223> OTHER INFORMATION: cell adhesive peptide

<400> SEQUENCE: 5

Cys Gly Gly Gly Gly Arg Gly Asp Ser Pro
1               5                   10
```

CLICK-CROSSLINKED HYDROGELS AND METHODS OF USE

CROSS-REFERENCE TO RELATED APPLICATIONS

This application is a continuation of U.S. application Ser. No. 15/301,466, filed on Oct. 3, 2016; which is a 35 U.S.C. § 371 national stage filing of International Application No. PCT/US2015/024523, filed on Apr. 6, 2015; which claims the benefit of priority of U.S. Provisional Application No. 61/975,375, filed on Apr. 4, 2014. The entire contents of each of the foregoing applications are hereby incorporated herein by reference.

GOVERNMENT SUPPORT

The invention was made with Government support under R01 HL069957 awarded by the National Institutes of Health and under W911NF-13-1-0242 awarded by the US Army Research Office. The Government has certain rights in the invention.

SEQUENCE LISTING

The instant application contains a Sequence Listing which has been submitted electronically in ASCII format and is hereby incorporated by reference in its entirety. Said ASCII copy, created on Sep. 2, 2020, is named 117823-09903_SL.txt and is 1,182 bytes in size.

BACKGROUND OF THE INVENTION

A hydrogel is a polymer gel comprising a network of crosslinked polymer chains. The network structure of hydrogels allows them to absorb significant amounts of water. Some hydrogels are highly stretchable and elastic; others are viscoelastic. Uses of hydrogels include cell delivery vehicles, cancer vaccines, tissue engineering (e.g., as scaffolding), and protein/small molecule delivery vehicles. Hydrogels are also useful as structural materials. Some existing hydrogels are formed by crosslinking polymers via a noncovalent bond, such as an ionic bond, e.g., through calcium crosslinking. Hydrogels created by noncovalent bonds may not be as tough or stable long term as hydrogels created by covalent bonds. However, the existing chemistry used to create hydrogels with polymers linked by covalent bonds is complex and costly. The chemical reactions are difficult to control with respect to the reaction side reactions, cross reactivity, and obtaining hydrogels with the desired physicochemical/mechanical properties, such as elasticity, strength, swelling extent, and degradation rate. Some of the existing hydrogels also exhibit cytotoxicity and/or the polymerization and crosslinking of the hydrogel cannot be created in the presence of living cells without causing significant cell death.

SUMMARY OF THE INVENTION

We recognized a need for covalent crosslinked hydrogels that are capable of being created using finely tunable and simple chemical reactions that are nontoxic to cells, that can occur at a rapid rate under biological conditions, that are more stretchable and/or stronger than currently existing hydrogels, and that are capable of being produced in a cost-effective way. Our invention addresses these needs. In broad aspect, this disclosure provides novel bioorthogonal pair of functional groups that react via click chemistry to form crosslinkers that can be used to form biocompatible hydrogels.

Thus, in one aspect, the disclosure provides a hydrogel comprising a first polymer and a second polymer, where the first polymer is connected to the second polymer by linkers of formula (A):

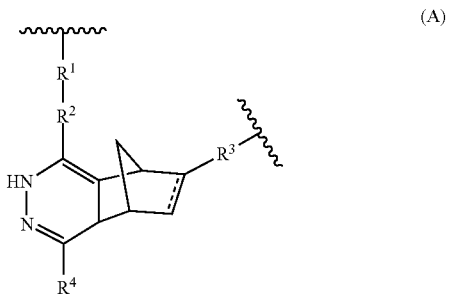

(A)

wherein
bond $\equiv$ is a single or a double bond;
$R^1$ is $-C_0$-$C_6$alkyl-$NR^{2N}-$, $-C_0$-$C_6$alkyl-O—, or $-C_0$-$C_3$alkyl-C(O)—;
$R^2$ is a bond, aryl, or heteroaryl, wherein aryl and heteroaryl are optionally substituted with halogen, hydroxy, $C_1$-$C_6$alkyl, $C_1$-$C_6$alkoxy, ($C_1$-$C_6$alkyl)amino, or di($C_1$-$C_6$alkyl)amino;
$R^3$ is $-C_0$-$C_6$alkyl-$NR^{2N}-$, $-C_0$-$C_6$alkyl-O—, or $-C_0$-$C_3$alkyl-C(O)—; and
$R^4$ is hydrogen, $C_1$-$C_6$alkyl, aryl, or heteroaryl, wherein aryl and heteroaryl are optionally substituted with halogen, hydroxy, $C_1$-$C_6$alkyl, $C_1$-$C_6$alkoxy, ($C_1$-$C_6$alkyl)amino, or di($C_1$-$C_6$alkyl)amino.

In one embodiment, the hydrogel of the disclosure is wherein the linkers of formula (A) are of the form of formula (I):

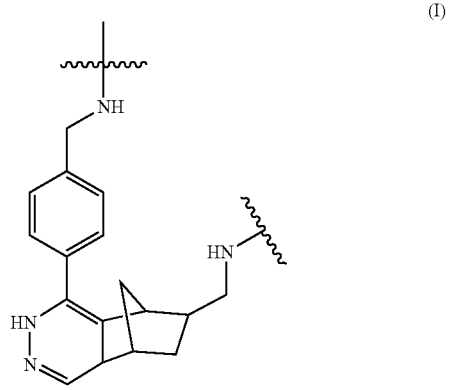 [SMILES: *NCc1ccc(C2=C3C(C=NN2)C2CC(CN*)C3C2)cc1]

(I)

or by formula (II):

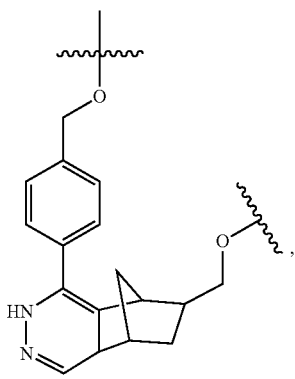

or by formula (III):

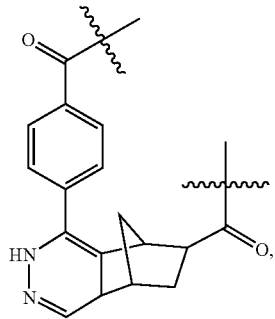

wherein the linkers of formula (I), (II), or (III) are optionally substituted at any suitable position.

In one embodiment, the linkers of formula (A) are wherein bond === is a single bond. In another embodiment, bond === is a double bond.

Another embodiment provides the linkers of formula (A) according to any preceding embodiment, wherein $R^1$ is
 a. $-NR^{2N}-$, $-C_1-C_6$ alkyl-$NR^{2N}$, $-O-$, $-C_1-C_6$alkyl-O$-$, $-C(O)-$, or $-C_1-C_3$alkyl-C(O)$-$;
 b. $-C_0-C_6$ alkyl-$NR^{2N}-$;
 c. $-C_1-C_6$ alkyl-$NR^{2N}-$;
 d. $-C_1-C_3$ alkyl-$NR^{2N}-$;
 e. -methyl-NH— or -pentyl-NH—;
 f. $-C_0-C_6$ alkyl-O—;
 g. $-C_1-C_6$ alkyl-O—;
 h. $-C_1-C_3$ alkyl-O—;
 i. -methyl-O— or -pentyl-O—;
 j. $-C_0-C_3$ alkyl-C(O)—;
 k. $-C(O)-$;
 l. -methyl-C(O)—;
 m. the same as $R^3$.

Another embodiment provides the linkers of formula (A) according to any preceding embodiment, wherein $R^2$ is a bond.

In one embodiment, the linkers of formula (A) according to any preceding embodiment are those wherein $R^2$ is
 a. aryl or heteroaryl, each optionally substituted;
 b. optionally substituted aryl;
 c. phenyl;
 d. optionally substituted heteroaryl; or
 e. pyridyl, pyrimidyl, or pyrazinyl.

Another embodiment provides the linkers of formula (A) according to any preceding embodiment, wherein $R^3$ is
 a. $-NR^{2N}-$, $-C_1-C_6$ alkyl-$NR^{2N}-$, $-O-$, $-C_1-C_6$ alkyl-O—, $-C(O)-$, or $-C_1-C_3$alkyl-C(O)—;
 b. $-C_0-C_6$ alkyl-$NR^{2N}-$;
 c. $-C_1-C_6$ alkyl-$NR^{2N}-$;
 d. $-C_1-C_3$ alkyl-$NR^{2N}-$;
 e. -methyl-NH— or -pentyl-NH—;
 f. $-C_0-C_6$ alkyl-O—;
 g. $-C_1-C_6$ alkyl-O—;
 h. $-C_1-C_3$ alkyl-O—;
 i. -methyl-O— or -pentyl-O—;
 j. $-C_0-C_3$ alkyl-C(O)—;
 k. $-C(O)-$;
 l. -methyl-C(O)—; or
 m. the same as $R^1$.

In one embodiment, the linkers of formula (A) according to any preceding embodiment are those wherein $R^4$ is hydrogen.

In one embodiment, the linkers of formula (A) according to any preceding embodiment are those wherein $R^4$ is
 a. $C_1-C_6$ alkyl, aryl, or heteroaryl, wherein aryl and heteroaryl are optionally substituted;
 b. aryl or heteroaryl, wherein aryl and heteroaryl are optionally substituted;
 c. optionally substituted aryl;
 d. phenyl;
 e. optionally substituted heteroaryl; or
 f. pyridyl, pyrimidyl, or pyrazinyl.

Another embodiment provides the linkers of formula (A) according to any preceding embodiment, wherein $R^4$ is $C_1-C_6$ alkyl, $C_1-C_3$ alkyl, or methyl.

In some embodiments, the hydrogel comprises a plurality of linkers of formula (A); or formula (I), formula (II), or formula (III).

The invention also includes a hydrogel comprising an interconnected network of a plurality of polymers, e.g., including a first polymer and a second polymer. For example, the polymers are connected via a plurality of linkers of formula (A), or of formula (I), formula (II), or formula (III).

Some embodiments of the disclosure provide hydrogels wherein the first polymer and the second polymer are independently soluble polymers. In other embodiments, the first polymer and the second polymer are independently water-soluble polymers.

In some cases, the concentration of crosslinks per hydrogel (e.g., where each crosslink comprises formula I) is at least about 10% (w/w), e.g., at least about 10%, about 15%, about 20%, about 30%, about 40%, about 50%, about 60%, about 70%, about 80%, about 90%, about 95%, about 97%, about 99%, or about 100% (w/w).

The first polymer and the second polymer can be the same or different. In some embodiments, the first polymer and the second polymer are the same type of polymer. In other embodiments, the first polymer and/or the second polymer comprise a polysaccharide. For example, the first polymer and the second polymer can both comprise a polysaccharide. In some embodiments, the first polymer and/or the second polymer are independently selected from the group consisting of alginate, chitosan, polyethylene glycol (PEG), gelatin, hyaluronic acid, collagen, chondroitin, agarose, polyacrylamide, and heparin. In some embodiments, the first polymer and the second polymer are the same polymer independently selected from the group consisting of alginate, chitosan, polyethylene glycol (PEG), gelatin, hyaluronic acid, collagen, chondroitin, agarose, polyacrylamide, and heparin.

Some embodiments of the disclosure provide hydrogels wherein the first polymer and the second polymer are independently selected from group consisting of alginate, chitosan, and gelatin. In one embodiment, the first polymer and the second polymer are independently alginate. In another embodiment, the first polymer and the second polymer are independently chitosan. In another embodiment, the first polymer and the second polymer are independently gelatin.

In some embodiments, the first polymer and/or the second polymer is modified by a cell adhesive peptide, e.g., an extracellular cell matrix (ECM) component. In one embodiment, the first and/or second polymer so-modified is alginate. The cell adhesive peptide can comprise, for example, the amino acid sequence arginine-glycine-aspartate (RGD). Examples include the amino acid sequence arginine-glycine-aspartate-cysteine (RGDC) (SEQ ID NO: 1) and arginine-glycine-aspartate-serine (RGDS) (SEQ ID NO: 2). In other examples, the cell adhesive peptide comprises the amino acid sequence of lysine-glutamine-alanine-glycine-aspartate-valine (KQAGDV) (SEQ ID NO: 3) or valine-alanine-proline-glycine (VAPG) (SEQ ID NO: 4). In some examples, the cell adhesive peptide is CGGGGRGDSP (SEQ ID NO: 5). Other cell adhesive peptides may be used based on the desired application and will be apparent to one of skill in the art.

In some cases, the cell adhesive peptide is covalently linked to the polymer via a thiol-ene reaction, e.g., via thiol-ene photochemistry. For example, the cell adhesive peptide can be covalently linked to the polymer (e.g., alginate) prior to or following crosslinking of the polymers to form a hydrogel. Such use of thiol-ene reaction to covalently like the cell adhesive peptide to the polymer is significantly faster and more efficient than the previously disclosed methods, such as methods using of carboxyl activating agents (e.g., EDC) to couple the peptide to the polymer.

In some examples, the hydrogel is elastic. For example, the Young's modulus of the hydrogel of the disclosure can be about 50 to about 50,000 Pa, e.g., about 50 to about 500 Pa, or about 50 to about 1,000 Pa, or about 50 to about 5,000 Pa, or about 50 to about 10,000 Pa, or about 500 to about 50,000 Pa, or about 500 to about 10,000 Pa, or about 500 to about 5000 Pa, or about 500 to about 1,000 Pa, or about 1,000 to about 50,000 Pa, or about 1,000 to about 10,000 Pa, or about 1,000 to about 5,000 Pa, or about 50 to about 20,000 Pa, or about 500 to about 20,000 Pa, or about 1,000 to about 20,000 Pa, or up to about 40,000 Pa, or up to about 30,000 Pa, or up to about 20,000 Pa.

In some embodiments, the hydrogel further comprises a cell, a biological factor, and/or a small molecule.

Exemplary cells include myoblasts for muscle regeneration, repair or replacement; hepatocytes for liver tissue regeneration, repair or organ transplantation, chondrocytes for cartilage replacement, regeneration or repair, pancreatic islets (e.g., for treatment of diabetes), and osteoblasts for bone regeneration, replacement or repair, various stem cell populations (embryonic stem cells differentiated into various cell types), bone marrow or adipose tissue derived adult stem cells, cardiac stem cells, pancreatic stem cells, endothelial progenitors and outgrowth endothelial cells, mesenchymal stem cells, hematopoietic stem cells, neural stem cells, satellite cells, side population cells, differentiated cell populations including osteoprogenitors and osteoblasts, chondrocytes, keratinocytes for skin, tenocytes for tendon, intestinal epithelial cells, endothelial cells, smooth muscle cells and fibroblasts for tissue or organ regeneration, repair or replacement and/or for DNA delivery. Preferably, the cells are mammalian, e.g., human; however, the system is also adaptable to other eucaryotic animal cells, e.g., canine, feline, equine, bovine, and porcine as well as prokaryotic cells such as bacterial cells.

A "biological factor" is a molecule having some sort of in vitro or in vivo biological activity. In some examples, the biological factor is a protein (e.g., peptide, polypeptide, antibody, or fragment thereof), nucleic acid (e.g., DNA, RNA, modified DNA or RNA, or aptamer), lipid (e.g., phospholipid), or carbohydrate (e.g., polysaccharide or proteoglycan).

Some biological factors are capable of maintaining cell viability, promoting cell proliferation, or preventing premature terminal differentiation of cells. Such biological factors are used alone or in combination to achieve the desired result.

Biological factors suitable for use in the present invention include, but are not limited to: growth factors, hormones, neurotransmitters, neurotransmitter or growth factor receptors, interferons, interleukins, chemokines, cytokines, colony stimulating factors, chemotactic factors, MMP-sensitive substrate, extracellular matrix components; such as growth hormone, parathyroid hormone (PTH), bone morphogenetic protein (BMP), transforming growth factor-α (TGF-α), TGF-β1, TGF-β2, fibroblast growth factor (FGF), granulocyte/macrophage colony stimulating factor (GMCSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin and vascular endothelial cell growth factor (VEGF). Splice variants of any of the above mentioned proteins, and small molecule agonists or antagonists thereof that may be used advantageously to alter the local balance of pro and anti-migration and differentiation signals are also contemplated herein.

Examples of cytokines as mentioned above include, but are not limited to IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-γ (γ-IFN), IFN-α, tumor necrosis factor (TNF), TGF-β, FLT-3 ligand, and CD40 ligand.

Suitable biological factors useful in accordance with the invention also include but are not limited to DNA molecules, RNA molecules, antisense nucleic acids, ribozymes, plasmids, expression vectors, marker proteins, transcription or elongation factors, cell cycle control proteins, kinases, phosphatases, DNA repair proteins, oncogenes, tumor suppressors, angiogenic proteins, anti-angiogenic proteins, cell surface receptors, accessory signaling molecules, transport proteins, enzymes, anti-bacterial agents, anti-viral agents, antigens, immunogens, apoptosis-inducing agents, anti-apoptosis agents, and cytotoxins.

The disclosure also features a method for preparing a hydrogel comprising:

a) providing a first polymer comprising a tetrazine moiety and a second polymer comprising at least one norbornene moiety. The number of tetrazine moieties in the first polymer (denoted by 't' in the examples below) can be any integer between 1 and 100,000:

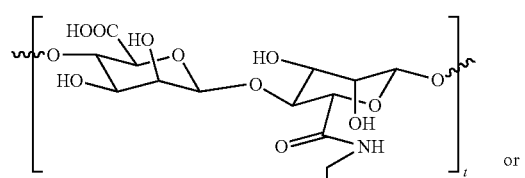

or

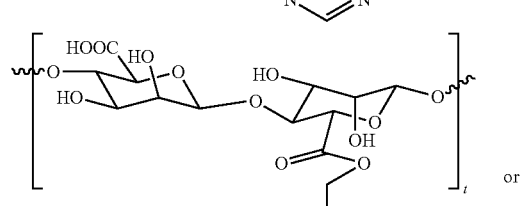

or

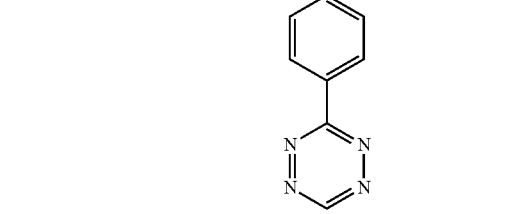

R = H or C(O)CH₃

The number of norbornene moieties in the second polymer (denoted by 'n' in the examples below) can be any integer between 1 and 100,000:

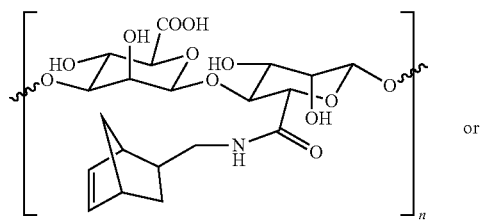

or

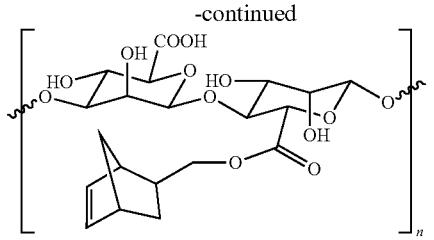

or

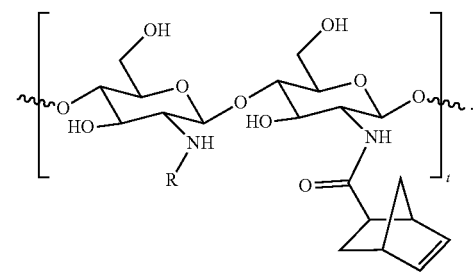

R = H or C(O)CH₃ b) contacting the second polymer with the first polymer to form a cross-linked polymer having crosslinks of formula (A). In one embodiment, the crosslinks of formula (A) are of the form of formula (I), (I)

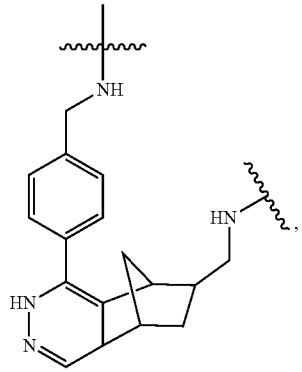

or formula (II), (II)

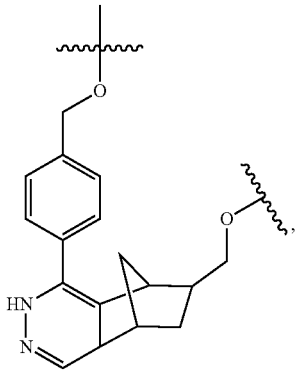

or formula (III):

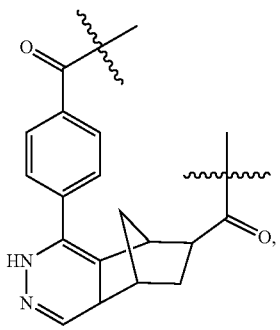

wherein the linkers of formula (I), (II), or (III) are optionally substituted at any suitable position.

In some cases, each molecule of the first polymer comprises about 1-50,000 tetrazine moieties, e.g., about 1-10,000, about 1-5000, about 1-1000, about 5000-50,000, about 5000-10,000, about 1000-10,000, about 1000-5000, about 500-5000, about 500-1000, or about 1-500 tetrazine moieties. In some cases, each molecule of the second polymer comprises about 1-50,000 norbornene moieties, e.g., about 1-10,000, about 1-5000, about 1-1000, about 5000-50,000, about 5000-10,000, about 1000-10,000, about 1000-5000, about 500-5000, about 500-1000, or about 1-500 norbornene moieties. In some embodiments, step b) of the method comprises contacting a second polymer with a first polymer at a ratio of about 1:104 to about 10:1 (second polymer:first polymer). For example, the ratio of the second polymer to the first polymer is about 1:10, or about 1:9, or about 1:8, or about 1:7, or about 1:6, or about 1:5, or about 1:4, or about 1:3, or about 1:2, or about 1:1, or about 2:1, or about 3:1, or about 4:1, or about 5:1, or about 6:1, or about 7:1, or about 8:1, or about 9:1, or about 10:1.

In some cases, the tetrazine moiety is coupled to the polymer by reacting the polymer with benzyl amine tetrazine and a coupling agent. In other examples, the tetrazine moiety is coupled to the alginate by reacting the polymer with benzyl alcohol tetrazine or benzoic acid tetrazine and a coupling agent. Exemplary coupling agents include, but are not limited to, 1-ethyl-3-(3-dimethylaminopropyl)carbodiimide (EDC), carbonyl diimidazole, N,N'-dicyclohexylcarbodiimide (DCC), N,N'-diisopropylcarbodiimide (DIC), and N,N,N',N'-tetramethyl-O-(1H-benzotriazol-1-yl)uronium hexafluorophosphate (HBTU).

In some cases, the norbornene moiety is coupled to the polymer by reacting the polymer with norbornene methanamine and a coupling agent. In other examples, the norbornene moiety is coupled to the polymer by incubating the polymer with norbornene methanol or norbornene carboxylic acid and a coupling agent. Exemplary coupling agents include, but are not limited to, EDC, carbonyl diimidazole, DCC, DIC, and HBTU. In some cases, N-Hydroxysuccinimide (NHS) is also included in the coupling reaction.

In some embodiments, the crosslinking capacity of the polymers has a maximum limit based on the degree of substitution of functional groups (e.g., norbornene and tetrazine) on the polymer(s). The crosslinking capacity can be characterized and measured, for example, mechanically by demonstrating that higher theoretical crosslinking density (e.g., the degree of substitution or the ratio of the first polymer:the second polymer) results in a stiffer or more highly crosslinked network of polymers in the hydrogel.

In some embodiments of the method, the crosslinking reaction proceeds as a spontaneous chemical reaction, such as with no input of light, heat, radicals needed. The crosslinking reaction can occur in water, in aqueous buffers or cell culture media (e.g., phosphate buffered saline, Hank's balanced salt solution, Dulbecco's Modified Eagle Medium, and the like), or in organic solvents (e.g., methanol, ethanol, dichloromethane, dimethylformamide, and the like). In addition, the crosslinking reaction can occur at a wide range of temperatures, such as about −80° C. to at least about 50° C., about −80° C., about −20° C., about 4° C., about 22° C., about 37° C., or about 50° C. In some examples, the crosslinking reaction occurs at a usable range of temperature and conditions for forming hydrogels and occurs without the input of external energy.

In some embodiments of the method, after crosslinking, unreacted norbornene and/or tetrazine remain on the polymers. In some cases the unreacted norbornene and/or tetrazine functional groups on the crosslinked hydrogel can be used for post-crosslinking reaction modification of the gel. The amount of unreacted norbornene and/or tetrazine on the polymers can be modulated by varying the ratios of the first polymer to the second polymer used during the crosslinking reaction.

The disclosure also features a method for preparing a hydrogel comprising:
a) providing a first polymer comprising a diene moiety and a second polymer comprising at least one dienophile moiety, wherein the diene is selected from:

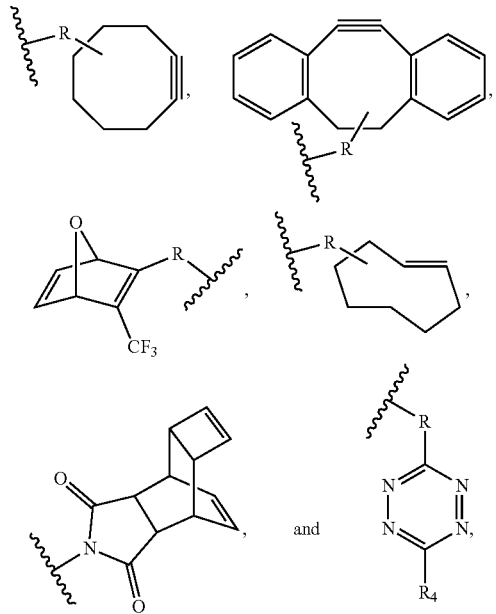

wherein R is a suitable spacer for linking to the first polymer, and $R^4$ is as defined above;
and the dienophile is selected from:

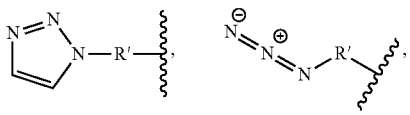

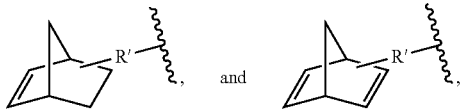

wherein R' is a suitable spacer for linking to the second polymer; and b) contacting the second polymer with the first polymer to form a cross-linked polymer.

In one embodiment, the disclosure provides a hydrogel prepared by the above method, comprising a first polymer and a second polymer, wherein the first polymer is connected to the second polymer by linkers resulting in Diels-Alder addition of a diene and dienophile moiety, wherein the diene is selected from:

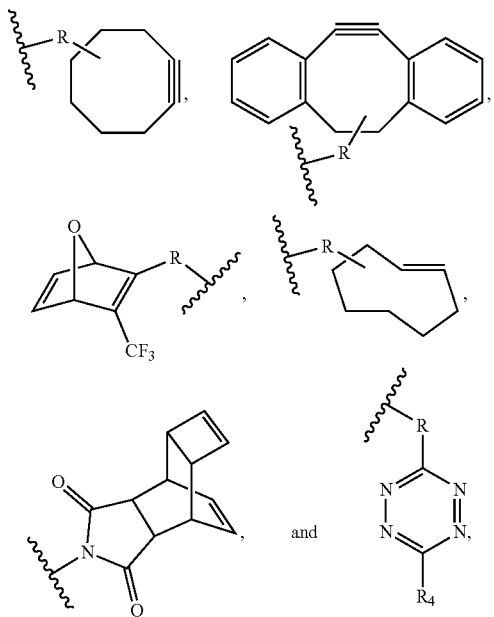

wherein R is a suitable spacer for linking to the first polymer, and $R^4$ is as defined above; and the dienophile is selected from:

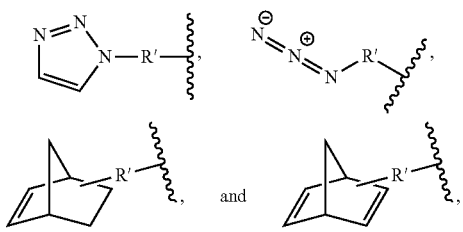

wherein R' is a suitable spacer for linking to the second polymer.

In one embodiment, the hydrogel is wherein R is $R^1$-$R^2$ moiety, wherein $R^1$ and $R^2$ are as defined above; and R' is $R^3$, wherein $R^3$ is as defined above.

The disclosure also provides a method of regenerating a tissue in a subject in need thereof comprising administering a hydrogel described herein further comprising cells to the subject. For example, the cells can be mammalian cells, and the tissue a mammalian tissue. In some embodiments, the mammalian cell is of the same type as the tissue to be regenerated. In other embodiments, the mammalian cell is a stem cell. Embodiments of the method include contacting a mammalian tissue with the hydrogel, where the hydrogel further comprises a first component that temporally regulates egress of the cell from the hydrogel and/or a second component that spatially regulates egress of the cell from the hydrogel.

In another example, a method of regenerating a target tissue of a mammal comprises providing a hydrogel described herein, where the hydrogel comprises a mammalian cell immobilized within the hydrogel (i.e., the mammalian cell remains within the hydrogel for an extended period of time without exiting the hydrogel). The method includes contacting a mammalian tissue with the hydrogel, where the mammalian cell is immobilized within the hydrogel, and where the hydrogel comprises a first component that temporally regulates egress of a cell of the mammalian cell from the hydrogel and a second component that spatially regulates egress of the mammalian cell from the hydrogel. In some embodiments the mammalian cell is a progeny cell. In some embodiments, the hydrogel remains stable and does not allow for host cell infiltration.

In one embodiment, the hydrogel described herein is useful as an immunoprotective barrier, e.g., for pancreatic islet transplantation. In some cases, pancreatic islet transplantation is a treatment for diabetes, e.g., Type I diabetes. Transplanted cells such as islets can be destroyed by immune reactions, and the hydrogels of the invention are capable of encapsulating cells such as islet cells prior to implantation/injection of the hydrogel. In this way, the hydrogels serve as an immunoprotective barrier in the body and minimize immune rejection of transplanted cells and tissues.

Additionally, the disclosure provides a method of modulating an activity of a cell in a mammal, comprising
(a) administering to a mammal a hydrogel described herein, where the hydrogel further comprises a recruitment composition incorporated therein or thereon; and
(b) contacting the cell with a deployment signal, wherein the deployment signal induces egress of the cell, and wherein the activity of the cell at egress differs from that prior to entering the hydrogel.

For example, the cell can be an immune cell and can be a dendritic cell, macrophage, T cell, or B cell.

In other embodiments, the hydrogels described herein are useful for long-term cell transplantation, i.e., encapsulated cells reside and proliferate in or on the hydrogel for at least 1 day (e.g., at least 1, 2, 3, 4, 5, 6, 7 days, or 1, 2, 3, 4, 5 weeks, or 1, 2, 3, 4, 5, 6, 7, 8, 9, 10, 11, 12 months, or 1, 2, 3, 4 years or more). For example, less than about 50% (e.g., less than about 50%, about 40%, about 30%, about 20%, about 10%, or less) of the encapsulated cells are released from the hydrogel into a surrounding tissue at least 1 day (e.g., at least 1, 2, 3, 4, 5, 6, 7 days, or 1, 2, 3, 4, 5 weeks, or 1, 2, 3, 4, 5, 6, 7, 8, 9, 10, 11, 12 months, or 1, 2, 3, 4 years or more) after administration of the hydrogel into a subject. In some cases, the hydrogels are capable of retaining the encapsulated cells in part due to the high level of stability (in structure and susceptibility to degradation) of the hydrogels.

The hydrogels and methods disclosed herein provide certain advantages. The click-crosslinked hydrogels of the invention are stronger and tougher than other types of hydrogels, e.g., hydrogels that are created via ionic crosslinks or a combination of ionic crosslinks and covalent crosslinks. The hydrogels of the disclosure are also robust and can maintain structural integrity for months in vivo. In contrast, the currently used cell compatible materials require ionic crosslinking (due to covalent bio-orthogonal issues given above), which does not maintain extended structural integrity. To date, there has been no disclosure of other covalent crosslinking strategy (for example, in alginate, gelatin, chitosan at least) that has the level of biocompatibility and/or bioorthogonality of the hydrogels disclosed herein.

Also, the hydrogels of described herein can be generated by crosslinking polymers in the presence of cells and do not necessarily have to be crosslinked and formed prior to introduction of cells into the hydrogel. In addition, the hydrogels described herein can be generated by crosslinking polymers in the presence of a wide range of biological factors (e.g., morphogens, cytokines, and proteins) without damaging these biological factors during the crosslinking process.

Additionally, the methods of the invention utilize click chemistry between norbornene and tetrazine functional groups, and this reaction has been shown to be rapid (gelling within an hour) and allows for in situ gelation of the disclosed biomaterials. Quite advantageously, the click chemistry between norbornene and tetrazine functional groups of the disclosure is employable and reliable in aqueous systems, such as biologically compatible conditions (e.g., pH, temperature, and water content of biological systems) and can be applied to a wide variety of biomaterials. Further, the click chemistry between norbornene and tetrazine of the disclosure infers solubility to hydrogels at physiological relevant pHs. For example, chitosan hydrogel is more soluble at physiological pH, whereas chitosan polymer is insoluble in water and requires solubilization in dilute acid, pH~2.

The methods of the invention can utilize one type of polymer, which provides more control over the assembly of the hydrogel and improved control over the crosslinking process, such as by controlling the percentage of tetrazine and norbornene side chains that are able to react with each other to form a hydrogel with the desired physicochemical and mechanical properties. In contrast, prior art covalent crosslinking strategies use biomaterials that can cross-react with cells or biological agents, or require polymerization initiators that can damage these materials. Covalent cross-linking according to the methods disclosed herein can be accomplished in the presence of cells and biological factors without altering or otherwise damaging them.

Also, the methods of the invention provide improved control over mechanical properties of the hydrogel (e.g., elasticity and strength, swelling ratios, and degradation profiles). These hydrogel mechanical characteristics can be tuned through manipulation of the polymer molecular weight(s), degree of click substitution, and/or stoichiometry of the click chemistry components. Another advantage of the methods and hydrogels is the ability to utilize non-reacted functional groups on the polymer(s) to covalently couple desired agents (e.g., cell adhesive peptides) after the hydrogel has been synthesized. Yet another advantage is the ability of the polymers to be crosslinked in situ to form the click cross-linked hydrogel without the need for external coupling agents or catalysts. This is especially advantageous for the formation and use of injectable hydrogels, i.e., hydrogels that are injectable as a flowable composition (e.g., a liquid) but that form a gel in the body after injection. The conjugation approach of the disclosure expands the versatility of biomaterial hydrogels.

Additionally, some previously available gels are based on 4-arm PEG-plus-peptide based systems. Our disclosure advantageously provides a one-component system (e.g., an alginate system or a chitosan system or a gelatin system), which is simpler and cheaper than other systems such as the PEG-peptide systems. This is in part because the polymer (e.g., alginate, gelatin, or chitosan) is inexpensive and in some embodiments can be the single base polymer for both of the two components of the hydrogels of the invention. Also, the disclosure provides the first demonstration of a tetrazine-norbornene click-chemistry crosslinked polysaccharide material. Moreover, the crosslinking reaction described herein can take place at a wide range of temperatures and conditions, which provides a robustness that allows for the generation of hydrogels/cryogels with similar and/or better performance than those previously available, including, for example, the ability to encapsulate more molecules and/or drugs in the gel than previously possible while keeping the cost and complexity to a minimum.

In the methods of the disclosure, norbornene can be efficiently (e.g., >95%) conjugated to thiol containing small molecules, polymers, peptides and proteins (through cysteines) in minutes via photoinitiated radical reaction. By contrast, prior art methods require extended reaction times (often overnight) with very low efficiency (e.g., less than 40%). The norbornene conjugate can be incorporated into gels in a homogenous manner through the methods of the disclosure. Further, conjugation of amine, thiol, hydroxyl, or carboxylic acid containing molecules (small molecules, peptides, proteins, etc.) can allow for the homogenous covalent crosslinking of these molecules to the hydrogels during gelation for either permanent or hydrolyzable biomaterials.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

BRIEF DESCRIPTION OF THE DRAWINGS

FIG. 9 (top) shows that 3T3 fibroblasts retained high viability after 3D encapsulation in click crosslinked gelatin with an increase in metabolic activity over a three day culture period. Bottom figure shows that encapsulated NIH/3T3 cells rapidly assume a spread morphology with encapsulation in click crosslinked gelatin after one day (cell length: 80±6 µm), whereas cells treated with broad-spectrum matrix metalloproteinase (MMP)-inhibitor marimastat do not assume a spread morphology (cell length: 16±2 µm).

DETAILED DESCRIPTION OF THE INVENTION

Figure 1:
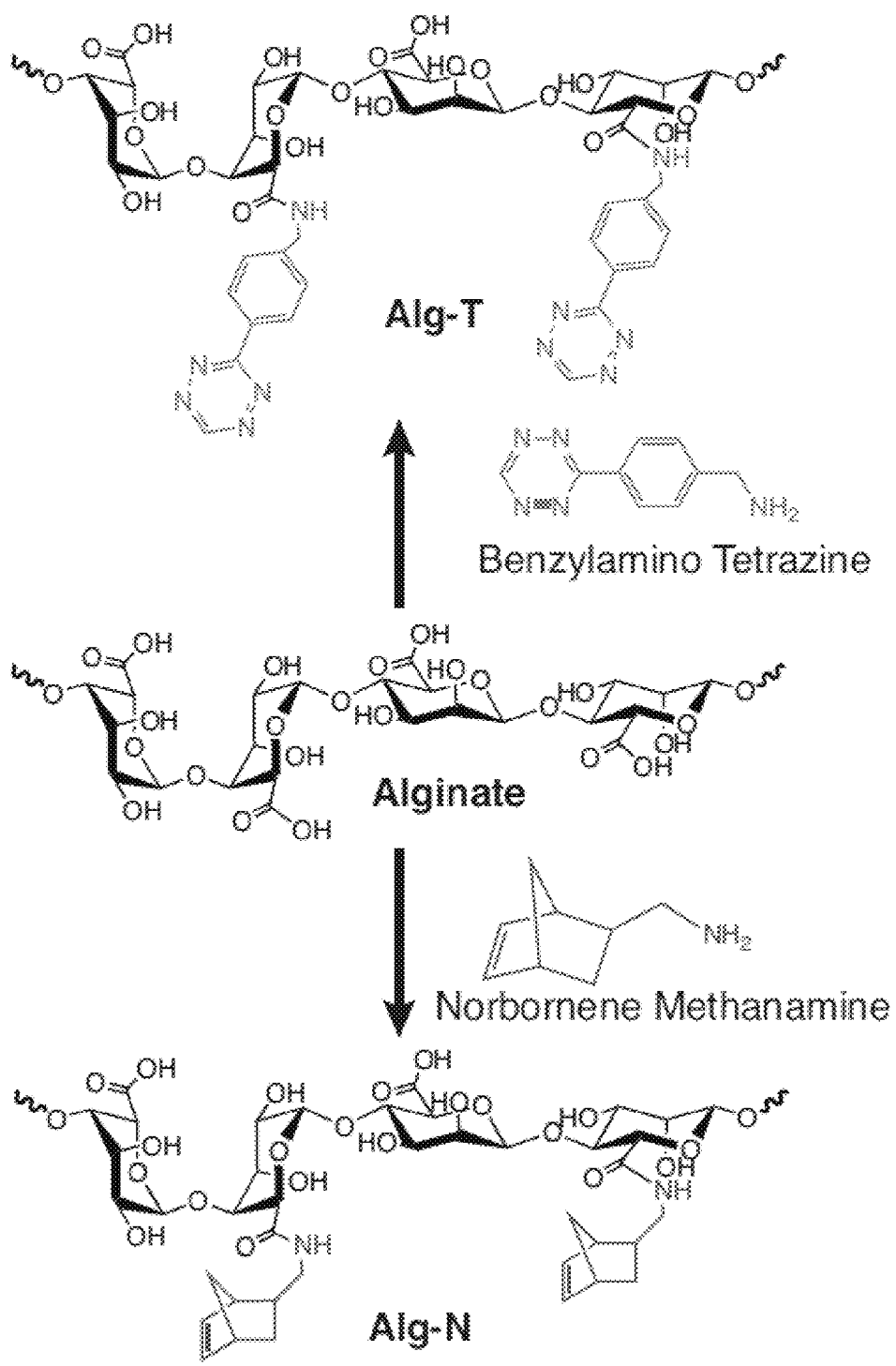
FIG. 1 is a schematic showing fabrication of click alginate hydrogels. In the figure aqueous carbodiimide chemistry is used to modify alginate backbone carboxylic acids with tetrazine or norbornene, resulting in Alg-T or Alg-N polymers respectively.

Before the disclosed methods and materials are described, it is to be understood that the aspects described herein are not limited to specific embodiments, apparatuses, or configurations, and as such can, therefore, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context dictates otherwise.

Ranges can be expressed herein as from "about" one particular value, and/or to "about" another particular value. When such a range is expressed, another aspect includes from the one particular value and/or to the other particular value. Similarly, when values are expressed as approximations by use of the antecedent "about," it will be understood that the particular value forms another aspect. It will be further understood that the endpoints of each of the ranges are significant both in relation to the other endpoint, and independently of the other endpoint. Quantitative values described herein using the modifier "about" can include ranges of 10% of the stated value.

As used herein, the term "aryl" represents an aromatic ring system having a single ring (e.g., phenyl) which is optionally fused to other aromatic hydrocarbon rings or non-aromatic hydrocarbon rings. "Aryl" includes ring systems having multiple condensed rings and in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. In certain examples, aryl groups include those having a first carbocyclic, aromatic ring fused to an aromatic or aliphatic heterocycle, for example, 2,3-dihydrobenzofuranyl. The aryl groups herein are unsubstituted or, when specified as "optionally substituted".

As used herein, the term "alkyl" means a saturated hydrocarbon having a designed number of carbon atoms, such as 1 to 6 carbons (i.e., inclusive of 1 and 6), 1 to 6 carbons, 1 to 3 carbons, or 1, 2, 3, 4, 5 or 6. Alkyl group may be straight or branched and depending on context, may be a monovalent radical or a divalent radical (i.e., an alkylene group). In the case of an alkyl or alkyl group having zero carbon atoms (i.e., "$C_0$alkyl"), the group is simply a single covalent bond if it is a divalent radical or is a hydrogen atom if it is a monovalent radical. For example, the moiety "—($C_0$-$C_6$alkyl)-O—" signifies connection of an oxygen through a single bond or an alkylene bridge having from 1 to 6 carbons and $C_0$-$C_3$alkyl represents a bond, methyl, ethyl, and propyl moieties. Examples of "alkyl" include, for example, methyl, ethyl, propyl, isopropyl, butyl, iso-, sec- and tert-butyl, pentyl, and hexyl.

The term "alkoxy" represents an alkyl group of indicated number of carbon atoms attached to the parent molecular moiety through an oxygen bridge. Examples of "alkoxy" include, for example, methoxy, ethoxy, propoxy, and isopropoxy.

The terms "halogen" or "halo" indicate fluorine, chlorine, bromine, and iodine.

As used herein, the term "heteroaryl" refers to an aromatic mono- or bi-cyclic ring system of 3-14 atoms ring system containing at least one heteroatom selected from nitrogen, oxygen and sulfur in an aromatic ring. Most commonly, the heteroaryl groups will have 1, 2, 3, or 4 heteroatoms. The heteroaryl may be fused to one or more non-aromatic rings, for example, cycloalkyl or heterocycloalkyl rings. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, pyrazinyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted".

As used herein the term "contacting" includes the physical contact of at least one substance to another substance, either directly or indirectly. An example of indirect contacting is injecting a hydrogel into a mammal to result in the hydrogel contacting a tissue.

As used herein the term "sufficient amount" and "sufficient time" includes an amount and time needed to achieve the desired result or results, such as to dissolve a portion of the polymer.

All percentages, ratios and proportions herein are by weight, unless otherwise specified. A weight percent (weight %, also as wt %) of a component, unless specifically stated to the contrary, is based on the total weight of the formulation or composition in which the component is included (e.g., on the total amount of the active material).

All temperatures are in degrees Celsius (° C.) unless otherwise specified.

In view of the present disclosure, the methods and compositions described herein can be configured by the person of ordinary skill in the art to achieve a desired goal. In general, the disclosed compositions and methods provide several unmet advantages. For example, the compositions and methods described herein provide a new method for making polysaccharide hydrogels using bioorthogonal chemistry. As the click alginate polymers and hydrogels are biocompatible and provide a bioorthogonal cross-linking reaction, there are many potential applications of these modified biopolymers, ranging from in vitro cell, protein, and drug encapsulation and release, to in vivo hydrogels with long-term stability. Though previous polymer systems may be capable of some of these applications, click polymers of the disclosure provide additional capabilities outside of canonical polymer hydrogels that were previous unattainable due to incompatible chemistries or contaminants. For instance, the hydrogels provided by the disclosure allow for the study of biological behavior of cells in 3 dimensions (3D)s, which provides a platform for observing spreading, proliferation, differentiation in a material system that does not interfere with the cells. Additionally, the polymers/hydrogels of the disclosure can be used in the field of super tough hydrogels that had been generated previously using a combination of ionic and click-crosslinked alginate polymers. See, e.g., Sun, et al. (2013). Highly stretchable and tough hydrogels. Nature, 489(7414), 133-136. The methods of the disclosure create a tougher alginate hydrogel compared to previous hydrogels, such as ionically crosslinked or ionic plus click-crosslinked hydrogels. Other engineering applications such as 3D cell/structure printing can also be developed with this system. For example, 3D printing can be accomplished by using the click alginate polymers as the "inks" that solidy and/or form structures once mixed and printed out of the printer. In some examples, during the printing process, cells and/or biological factors/small molecules can also be encapsulated within the network of polymers to form the hydrogel. Click alginate polymers are also useful, e.g., alone, as bulking agents. For example, the hydrogels of the disclosure can be applied (e.g., not in combination with other agents) for cosmetic and aesthetic applications, or in other situations where tissue bulking is needed for function such as incontinence treatment. For example, cosmetic uses include the treatment of wrinkles, the filling of small tissue defects with the hydrogels described herein, e.g., alginate gels in addition to or comprising fat forming cells (see, e.g., US 2013-0195764; WO 12/148684; WO 12/167230; and WO 12/167230, incorporated herein by reference). In some examples, the hydrogels of the disclosure are useful for tissue bulking for gastroesophageal reflux disease (GERD), incontinence treatment, and/or urinary reflux. In some cases, hydrogels are injected into the appropriate tissue site, where the hydrogel would provide expansion of the tissue and long-term maintenance of this expanded volume, in part due to the high level of stability of the hydrogel.

There are currently methods to generate polyethylene glycol (PEG)-based hydrogels. See, e.g., Alge, et al. (2013). Synthetically Tractable Click Hydrogels for Three-Dimensional Cell Culture Formed Using Tetrazine-Norbornene Chemistry. *Biomacromolecules,* 14(4), 949-953. However, while these PEG-based hydrogels are capable of encapsulating cells and patterning, this system has not been developed into any applications. Unlike the instant disclosure, to make the PEG-based hydrogels, Alge grafts tetrazine onto the PEG polymers, and then use a cleavable peptide bearing norbornene on each end to crosslink those polymers. In contrast, the click polymer system of the disclosure is a two-component system where the base polymer is the same, but has been modified differently to form the two components. This click polymer system of the disclosure is beneficial for significantly decreasing complexity and cost of the material system.

In some embodiments, polymers, e.g., alginate polymers, are modified with tetrazine or norbornene groups that can subsequently be covalently cross-linked to form click-cross-linked hydrogels, e.g., Click alginate hydrogels. Click-crosslinked hydrogels are capable of encapsulating cells, proteins, and other biological molecules with minimal damage. For example, the viability of a population of cells following encapsulation into a hydrogel described herein in at least about 10%, e.g., at least about 10%, or about 20%, or about 30%, or about 40%, or about 50%, or about 60%, or about 70%, or about 80%, or about 90%, or about 95% or greater. Viability of cells can be determined by standard methods in the art.

The cross-linking reaction has been previously shown by others to be highly specific, bio-orthogonal, and quick (see, e.g., Devaraj et al. Bioconjugate Chem. 19.12 (2008):2297-2299; Karver et al. Bioconjugate Chem. 22.11 (2011):2263-2270; and Alge et al. Biomacromol. 14.4 (2013):949-953), allowing for incorporation of cells with high postencapsulation viability.

Exemplary polymers include but are not limited to alginate, chitosan, poly ethylene glycol (PEG), gelatin, hyaluronic acid, collagen, chondroitin, agarose, polyacrylamide, and heparin.

The first polymer and the second polymer may be formulated for specific applications by controlling the molecular weight, rate of degradation and method of scaffold formation. Coupling reactions can be used to covalently attach bioactive epitopes, such as the cell adhesion sequence RGD to the polymer backbone (for example, see modified alginate below). Differences in hydrogel formulation control the kinetics of hydrogel degradation. Release rates of pharmaceutical compositions, e.g., small molecules, morphogens, proteins, nucleic acids, or other bioactive substances, from alginate hydrogels is controlled by hydrogel formulation to present the pharmaceutical compositions in a spatially and temporally controlled manner. This controlled release eliminates systemic side effects.

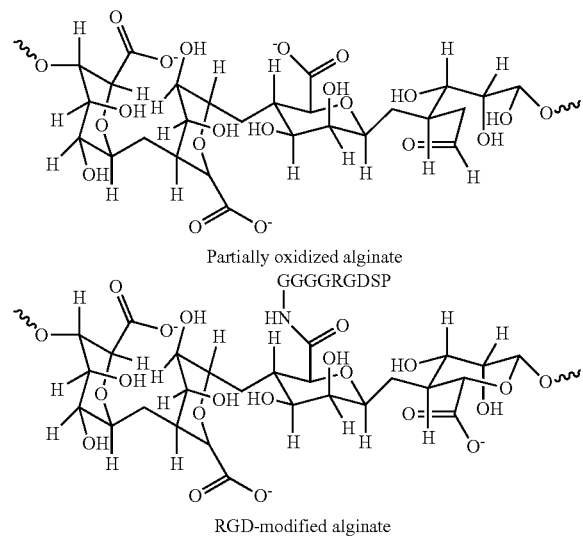

Partially oxidized alginate

RGD-modified alginate

Alginate molecules are comprised of (1-4)-linked β-D-mannuronic acid (M units) and a L-guluronic acid (G units) monomers, which can vary in proportion and sequential distribution along the polymer chain.

In a preferred embodiment, the first polymer and the second polymer are independently alginate, chitosan, or gelatin. In another embodiment, the first polymer and the second polymer are independently alginate. In another embodiment, the first polymer and the second polymer are independently chitosan. In another embodiment, the first polymer and the second polymer are independently gelatin.

For example, the polymers (e.g., alginates) of the hydrogel are about 50-100% crosslinked, e.g., at least about 50%, or about 60%, or about 70%, or about 80%, or about 90%, or more crosslinked. The polymer (e.g., alginate) can be oxidized, reduced, or neither, or a mixture thereof. In some cases, oxidized polymers or partially oxidized polymers are biodegradable. For example, hydrogels comprising oxidized or partially oxidized alginate are biodegradable.

Figure 2:
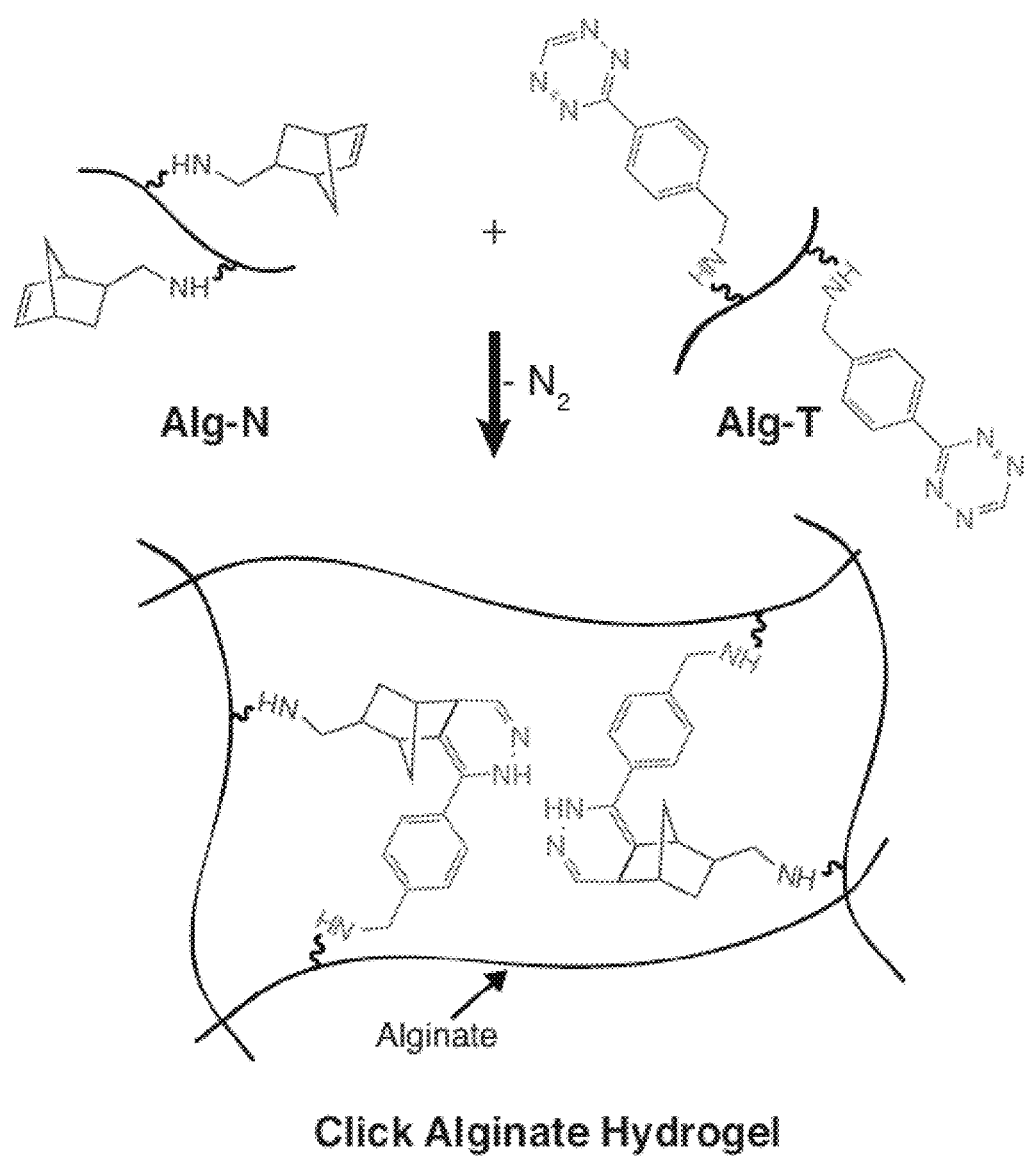
FIG. 2 is a schematic showing a click alginate polymer cross-linking reaction where Alg-T and Alg-N polymers are mixed together to create a covalently crosslinked click alginate hydrogel network, with the loss of $N_2$.

Methods of preparing a hydrogel described herein are also provided by the disclosure. For example, a schematic illustration a method for preparing a hydrogel is shown in FIGS. 1 and 2.

The mechanical properties of the hydrogels described herein, e.g., click alginate hydrogels or click gelatin hydrogels, can be tuned for a set polymer concentrations via the degree of substitution of norbornene or tetrazine groups on the polymer chains or the ratio of norbornene to tetrazine groups. This tuning allows for the creation of elastic hydrogels with Young's moduli ranging from about 50 to about 50,000 Pa.

In some cases, the hydrogels described herein are strong. For example, upon compression or dehydration, the hydrogel maintains structural integrity, i.e., after compression or dehydration, the hydrogel regains its shape after it is rehydrated or the shear forces of compression are removed/relieved. The hydrogel also maintains structural integrity in that it is flexible (i.e., not brittle) and does not break under sheer pressure.

The norbornene modified polymers (e.g., norbornene modified alginate) can also be modified with thiol-containing molecules or proteins via thiol-ene photochemistry either before or after crosslinking into a hydrogel. For example, the thiol-ene chemistry occurs before crosslinking. In such cases, the thiol reacts with all of the norbornene functional groups on the polymer(s). In other cases, there remain unreacted norbornene groups on the polymer(s) after reaction with the thiol. The reactivity can be controlled by varying the amount of thiol containing compound and the amount of polymer containing norbornene groups (e.g., incubating a smaller number of moles of thiol with a larger number of moles of polymer containing norbornene. Alternatively, reactivity can be controlled by varying the degree of substitution of the polymer(s) with norbornene groups and, e.g., incubating a smaller number of moles of thiol with a larger number of moles of total norbornene groups. In such a way, unreacted norbornene groups on the polymer after the thiol-ene chemical reaction are available to react with tetrazine in the crosslinking reaction. In some examples, the thiol does not react with the crosslinked norbornene-tetrazine product after gelation.

As used herein, the terms "tetrazine" and "tetrazine moiety" include molecules that comprise 1,2,4,5-tetrazine substituted with suitable spacer for linking to the polymer (e.g., alkylamines like methylamine or pentylamine), and optionally further substituted with one or more substituents at any available position. Exemplary tetrazine moieties suitable for the compositions and methods of the disclosure include, but are not limited to, the structures shown below (see, e.g., Karver et al. Bioconjugate Chem. 22(2011):2263-2270, and WO 2014/065860, both incorporated herein by reference):

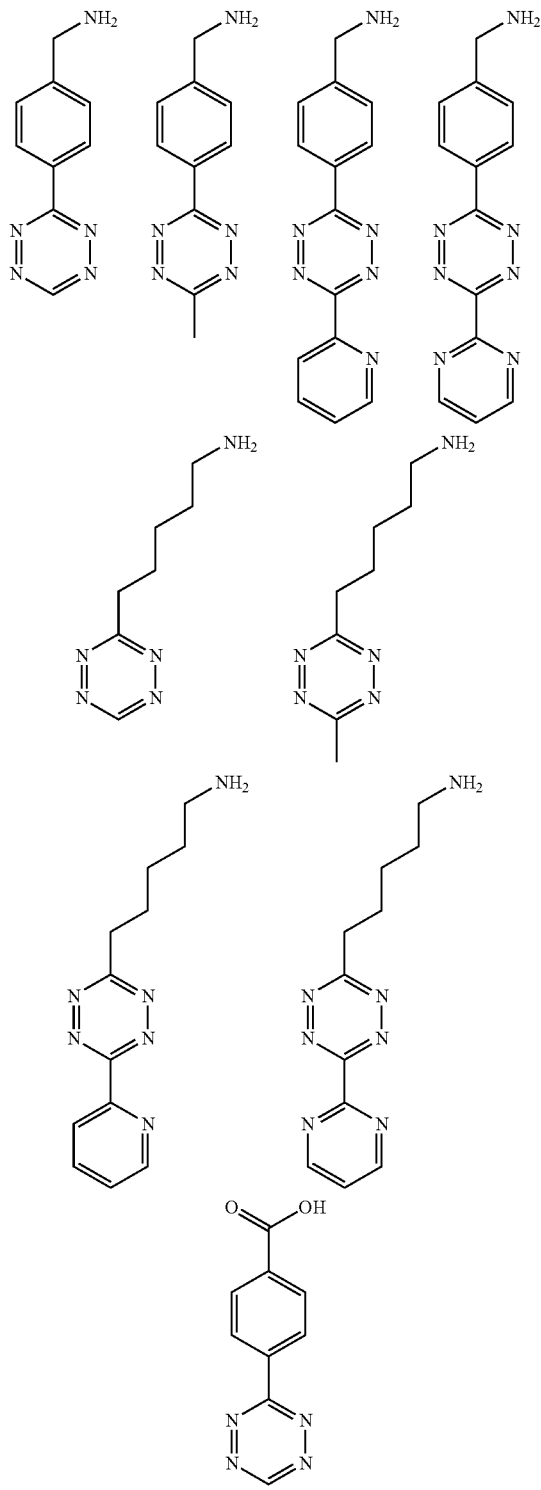

As used herein, the terms "norbornene" and "norbornene moieties" include but are not limited to norbornadiene and norbornene groups further comprising suitable spacer for linking to the polymer (e.g., alkylamines like methylamine or pentylamine), and optionally further substituted with one or more substituents at any available position. Such moieties include, for example, norbornene-5-methylamine and norbornadienemethylamine.

A variety of polymers suitable for the click conjugation of the disclosure allow for a drug delivery platform that can be used to configured for specific drug delivery goals through the material specific characteristics given herein. Exemplary applications include use as a dermal filler, in drug delivery, as a wound dressing, for postsurgical adhesion prevention, and for repair and/or regenerative medical applications such as cell therapy (e.g., immunoisolated cell therapy), gene therapy, tissue engineering, immunotherapy.

Finally, the hydrogels described herein are defect resistant, i.e., the durable gel is not prone to development of tears. But even if a defect arises, the gel maintains its toughness and does not fail.

An advantage of the hydrogels described herein is that they are biocompatible to cells (e.g., show lack of degradation and no inflammation in cells) over long periods of time, e.g., 3 days, 7 days, 14 days, 28 days 56 days, 112 days, or 224 days.

The biocompatible hydrogels described herein offer significant advantages, particularly in medical applications. For example, drug delivery hydrogels or cell delivery hydrogels that are used for muscle generation or regeneration are subject to application of energy/stresses. Because the hydrogels described herein are more mechanically robust, more durable, and are characterized by a higher fracture resistance compared to prior hydrogels, they are more suitable for such applications involving muscle tissue. Other applications are also improved with the use of the tough hydrogels. For example, materials used in surgical procedures (e.g., wraps, meshes), cartilage replacement, joint replacement, orthopedic/orthochondral defect repair (e.g., bone or cartilage fillers), spinal procedures (e.g., nuclear propulsus spinal surgery), ophthamological uses (e.g., optically-clear, flexible, durable lenses, contact lens or implantable lens), as well as non-medical uses (e.g., fillers in cosmetic surgical procedures).

In addition to clinical uses such as tissue repair and replacement, the hydrogels are also useful in non-medical settings, such as in fabrication of soft robotics that swim, crawl, fly, or squeeze through small spaces without breaking. The hydrogels are also useful to make actuators. Other examples include artificial muscles, tunable lenses, actuators and skins for soft robotics, encapsulate protecting layers, stretchable membranes for dielectric actuator, loud speaker membranes, multilayer systems, fiber reinforced tough hydrogel, particle reinforced tough gel as well as durable filtration systems.

Biological factors such as polynucleotides, polypeptides, or other agents (e.g., antigens) are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. The preparations herein can also be at least 75%, more preferably at least about 90%, and most preferably at least about 99%, by weight the compound of interest. For example, a purified compound is one that is at least about 90%, about 91%, about 92%, about 93%, about 94%, about 95%, about 98%, about 99%, or about 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents.

Similarly, by "substantially pure" is meant that a nucleotide, polypeptide, or other compound has been separated from the components that naturally accompany it. Typically, the nucleotides and polypeptides are substantially pure when they are at least about 60%, about 70%, about 80%, about 90%, about 95%, about 99%, or even 100%, by weight, free from the proteins and naturally-occurring organic molecules with they are naturally associated. Examples include synthesized compounds, recombinant compounds (e.g., peptides, proteins, nucleic acids) or purified compounds, such as purified by standard procedures including chromatographic methods.

An "isolated nucleic acid" is a nucleic acid, the structure of which is not identical to that of any naturally occurring nucleic acid, or to that of any fragment of a naturally occurring genomic nucleic acid spanning more than three separate genes. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybridgene, i.e., a gene encoding a fusion protein. Isolated nucleic acid molecules according to the present disclosure further include molecules produced synthetically, as well as any nucleic acids that have been altered chemically and/or that have modified backbones.

A "deployment signal" is a composition such as protein, peptide, or nucleic acid. For example, cells migrating into the hydrogel only encounter the deployment signal once they have entered the hydrogel. In some cases, the deployment signal is a nucleic acid molecule, e.g., a plasmid containing sequence encoding a protein that induces migration of the cell out of the hydrogel and into surrounding tissues. The deployment signal occurs when the cell encounters the plasmid in the hydrogel, the DNA becomes internalized in the cell (i.e., the cell is transfected), and the cell manufactures the gene product encoded by the DNA. In some cases, the molecule that signals deployment is an element of the hydrogel and is released from the hydrogel in delayed manner (e.g., temporally or spatially) relative to exposure of the cell to the recruitment composition. Alternatively, the deployment signal is a reduction in or absence of the recruitment composition. For example, a recruitment composition induces migration of cells into the hydrogel, and a reduction in the concentration or depletion, dissipation, or diffusion of the recruitment composition from the hydrogel results in egress of cells out of the hydrogel. In this manner, immune cells such as T cells, B cells, or dendritic cells (DCs) of an individual are recruited into the hydrogel, primed and activated to mount an immune response against an antigen-specific target. Optionally, an antigen corresponding to a target to which an immune response is desired is incorporated into or onto the hydrogel structure. Cytokines, such as granulocyte macrophage colony stimulating factor (GM-CSF) are also a component of the hydrogel to amplify immune activation and/or induce migration of the primed cells to lymph nodes. For example, vascular endothelial growth factor (VEGF) is useful to recruit angiogenic cells.

The disclosure will be further described in the following examples, which do not limit the scope of the disclosure described in the claims.

EXAMPLES

Example 1: 3-(p-benzylamino)-1,2,4,5 tetrazine synthesis 50 mmol of 4-(aminomethyl)benzonitrile hydrochloride and 150 mmol formamidine acetate were mixed while adding 1 mol of anhydrous hydrazine. The reaction was stirred at 80° C. for 45 minutes and then cooled to room temperature, followed by addition of 0.5 mol of sodium nitrite in water. 10% HCl was then added dropwise to acidify the reaction to form 3-(p-benzylamino)-1,2,4,5-tetrazine. The oxidized acidic crude mixture was then extracted with DCM. After discarding the organic fractions, the aqueous layer was basified with $NaHCO_3$, and immediately extracted again with DCM. The final product was then recovered by rotary evaporation, and purified by HPLC. All chemicals were purchased from Sigma-Aldrich.

Example 2: Click Alginate Polymer Synthesis

Click alginate biopolymers were modified with either 1-bicyclo[2.2.1]hept-5-en-2-ylmethanamine (Norbornene Methanamine; Matrix Scientific) or 3-(p-benzylamino)-1,2,4,5-tetrazine by first allowing high molecular weight alginate, $M_w$=265 kDa (Protanol LF 20/40; FMC Technologies) to dissolve in stirred buffer containing 0.1 M MES, 0.3 M NaCl, pH 6.5 at 0.5% w/v. Next, N-hydroxysuccinimide (NHS; Sigma-Aldrich) and 1-ethyl-3-(3-dimethylaminopropyl)-carbodiimide hydrochloride (EDC; Sigma-Aldrich) were added in 5× molar excess of the carboxylic acid groups of alginate. Either norbornene or tetrazine was then added at 1 mmol per gram of alginate to make Alg-N or Alg-T, respectively. The coupling reaction was stirred at room temperature for 24 hours, after which the reaction was quenched with hydroxylamine (Sigma-Aldrich) and dialyzed in 12-14 kDa MWCO dialysis tubing (Spectrum Labs) for 4 days against a decreasing salt gradient from 150 mM to 0 mM NaCl in $diH_2O$. The purified Alg-N and Alg-T polymers were treated with activated charcoal, sterile filtered (0.22 μm), and freeze-dried. This resulted in purified Alg-N or Alg-polymers with a 5% degree of substitution of the available carboxylic acid groups of alginate.

Example 3: Preparation and Characterization of Click Alginate Hydrogels

Click alginate hydrogels were prepared by first separately dissolving freeze-dried Alg-N and Alg-T polymers to final desired concentration (2-4% w/v) in Dulbecco's Modified Eagle Medium (DMEM; Gibco). For gelation kinetics measurements, Alg-N and Alg-T polymer solutions were mixed at a desired ratio (i.e., 0.5-4:1 N:T) and directly pipetted onto the bottom plate of a TA Instruments ARG2 rheometer equipped with 8 mm flat upper plate geometry. A Peltier cooler was used to control the temperature for temperature dependent experiments, and mineral oil was applied to the gel periphery to prevent the hydrogel from drying during testing. Hydrogel samples were subjected to 1% strain at 1 Hz, and the storage and loss moduli (G' and G") were monitored for 4 hours. For Young's modulus measurements click alginate hydrogels were formed under siliconized glass plates (Sigmacote; Sigma-Aldrich) with 2 mm spacers. After 2 hours of crosslinking at room temperature, cylindrical disks were punched using an 8 mm biopsy punch, transferred to DMEM, and swollen to equilibrium for 24 hours at 37° C. Swollen hydrogel sample dimensions were measured using calipers for volumetric swelling ratio measurements, and then subjected to unconfined compression testing (1 mm/min) using a 10 N load cell with no preload (Instron Model 3342). The Young's modulus, E, was calculated as the slope of the linear portion (first 10%) of the stress vs. strain curves.

To prepare click alginate polymers, norbornene or tetrazine groups were introduced to high molecular weight alginate biopolymers using conventional carbodiimide chemistry (FIG. 1). The degree of substitution of norbornene or tetrazine groups onto purified click alginate polymers was determined from $^1$H NMR spectra. A 5% degree of substitution of norbornene (Alg-N) or tetrazine (Alg-T) on alginate carboxyl groups was obtained using this method, and these batches of click alginate polymers were used for all subsequent experiments.

Figure 3A:
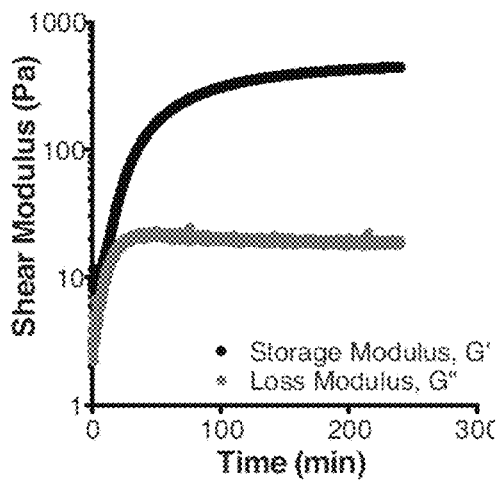
FIG. 3A illustrates representative in situ dynamic rheometry plot at 25° C. for 3% w/v click alginate at N:T=1, demonstrating modulus evolution with time.

To form click alginate hydrogels, Alg-N and Alg-T polymer solutions were prepared separately and mixed together to gel. Upon mixing of the two click alginate polymers, a stable gel was formed via an inverse electron demand Diels-Alder reaction between the two polymers, which releases nitrogen gas (FIG. 2). The nitrogen gas evolved from the crosslinking reaction does lead to the formation of a few small bubbles within the hydrogel. A stable gel was formed within 1 hour at 25° C. (FIG. 3A), though the gelation kinetics could be tuned by varying the temperature or initial degree of substitution of the click alginate polymers (data not shown). The gelation kinetics at 25° C. are favorable because it allows the user to easily achieve a well-mixed polymer formulation before gelation, a common challenge with other alginate hydrogel crosslinking methods.

Figure 3B:
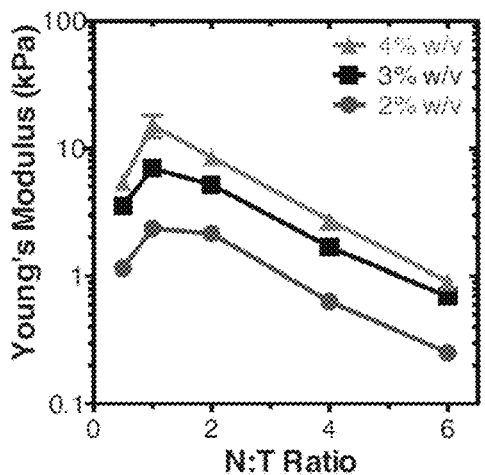
FIG. 3B illustrates compressive Young's modulus.

The mechanical properties of the extracellular matrix have been shown to affect cell fate and function in 2D and 3D environments. In order to tune mechanical properties over a wide range, click alginate polymers were mixed at different ratios of Alg-N and Alg-T (N:T ratio) for a given polymer concentration between 2 and 4% w/v. These click alginate hydrogel samples were subjected to unconfined compression tests resulting in a compressive Young's modulus that predictably increased with increasing polymer concentration, and decreased as the ratio between the polymers deviated from the stoichiometrically balanced N:T ratio of 1 (FIG. 3B). The ability to tune the mechanical properties of the resulting gel over a large range by simply changing the ratio of the two polymers allows control over gel stiffness while keeping other parameters such as polymer concentration, and ligand density constant which may be useful for studies of mechanobiology.

Figure 3C:
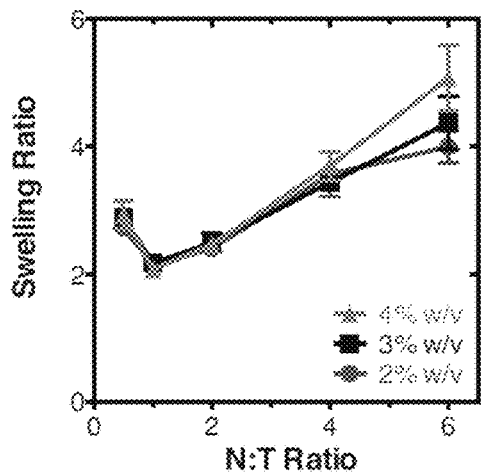
FIG. 3C illustrates volumetric swelling ratios for 2%, 3% and 4% w/v click alginate hydrogels at varying N:T ratio. Values represent mean and standard deviation (n=4).
Figure 4A:
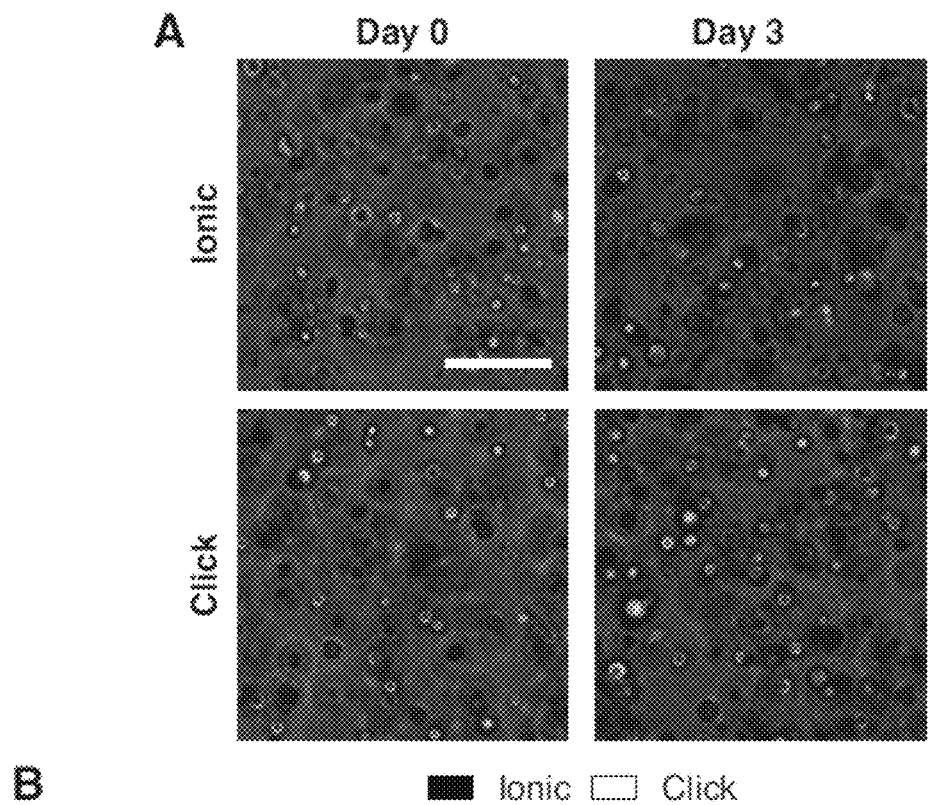
FIGS. 4A-B illustrate 3T3 fibroblast encapsulation in click crosslinked (2% w/v click crosslinked (N:T=1)) and ionically crosslinked alginate hydrogels stained with ethidium homodimer-1 (red) for dead cells at 4 hours and 3 days post encapsulation (scale bar=100 µm) (4A). Quantitative analysis of cell viability (Two-Way ANOVA with Sidak's post-hoc test, p<0.01, *p<0.001; Values represent mean and standard deviation, n=4) and overall metabolic activity as measured by reduction of AlamarBlue over time in culture (n=6) (4B).
Figure 4B:
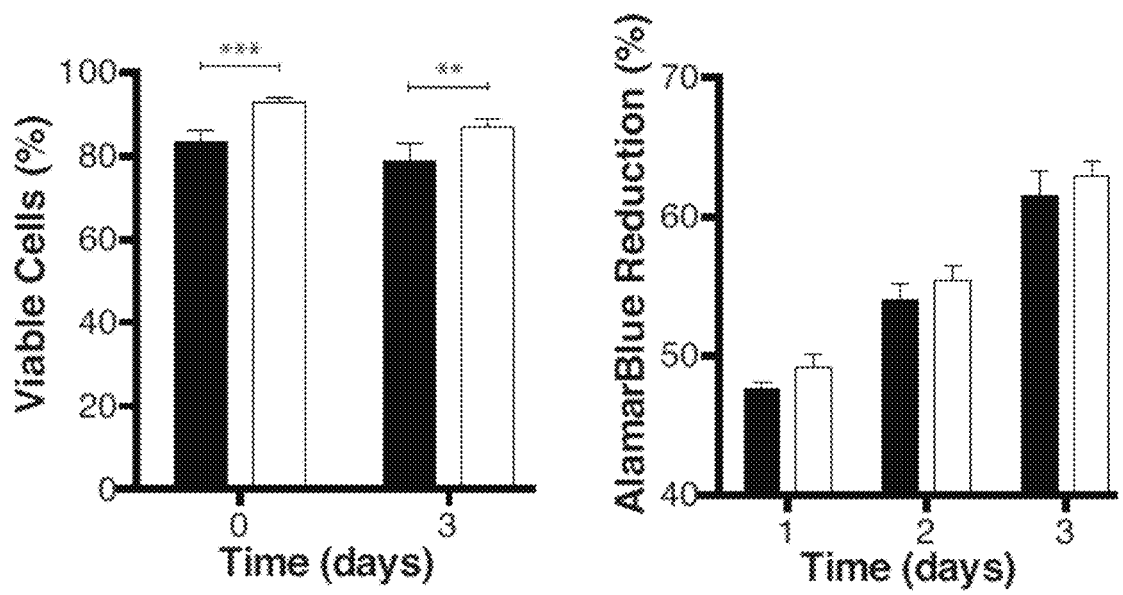

The swelling ratio of hydrogel systems can affect mechanical properties, mass transport, and the presentation of ligands on the gel surface. To investigate how volumetric swelling would change at different polymer concentrations and N:T ratios, click alginate hydrogels were made as previously described and allowed to swell for 24 hours at 37° C. The swollen volume was measured and compared to the casted volume (FIG. 3C). For a given polymer concentration, the volumetric swelling ratio increased as the N:T ratio deviated from 1, demonstrating an inverse relationship between mechanical properties and swelling ratio as expected. While the N:T ratio has a significant effect on the swelling ratio, the polymer concentration does not have a significant effect, indicating that the swelling ratio of click alginate is dominated by crosslink density rather than polymer concentration (data not shown).

Example 4: Viability of Cells Encapsulated in Click-Crosslinked Hydrogels

NIH 3T3 (ATCC) cells were transduced with lentivirus produced from an EGFP-containing lentiviral vector (pLCAG EGFP, Inder Verma lab, Addgene plasmid 14857) and were selected for 7 days in 1 µg/mL puromycin dihydrochloride (EMD Millipore). EGFP-expressing 3T3 fibroblast cells were cultured in DMEM supplemented with 10% (v/v) fetal calf serum, 100 U/mL penicillin, and 100 µg/mL streptomycin (Gibco) at 37° C., in a 5% $CO_2$ environment. Cells were passaged approximately twice per week.

For cell adhesion studies, slabs of click alginate hydrogels were modified with cell adhesion peptides as described above. 6 mm disks were punched, placed in DMEM, washed several times, and swollen for 4 hours prior to seeding with cells at $5 \times 10^4$ cells/mL at a depth of approximately 1 mm above the surface of the gel. Cells were given 24 hours to adhere and spread and then visualized via EGFP fluorescence using an epifluorescence microscope. EGFP images were used to quantify total cell area using ImageJ software. After 3 days of culture cells were fixed and stained using Alexa Fluor 594 phalloidin (Molecular Probes) and Hoescht 33342 (Molecular Probes) to visualize F-actin filaments and nuclei respectively. To visualize cell death, gels were incubated for 20 minutes with a 4 µM ethidium homodimer-1 (Molecular Probes) solution in Hanks Buffered Saline Solution (HBSS) and imaged using an epifluorescence microscope.

For cell encapsulation studies, Alg-N polymers were modified to have approximately 20 cell adhesive GGG-GRGDSP peptides (Peptide2.0) per alginate chain as previously described. 600 µm thick click alginate hydrogels at 2% w/v, N:T=1, were then made containing cells at $3 \times 10^6$ cells/mL. Ionically crosslinked hydrogels were similarly prepared at 2 w/v using the same cell density and backbone RGD modified Alg-N polymers, A $CaSO_4$ slurry (0.21 g $CaSO_4$/mL dd$H_2$O) at a final concentration of 2% w/v was used to crosslink the ionically crosslinked hydrogel samples so as to match the mechanical properties of the two substrates as closely as possible. To minimize the time in which cells did not have access to culture media, gels were allowed to crosslink at room temperature for 1 hour, after which 6 mm disks were punched and placed in culture medium where the crosslinking reaction was expected to proceed to completion.

Cells were retrieved from alginate hydrogels by digestion in a 5 U/mL alginate lyase (Sigma-Aldrich) solution in HBSS for 20 minutes. For viability testing, cells were stained with a Muse Count and Viability Kit and tested on a Muse Cell Analyzer (EMD Millipore). To assess total cell metabolic activity, gels were transferred to wells containing 10% AlamarBlue (AbD Serotec) in cell culture medium and incubated for 4 hours. The reduction of AlamarBlue was assessed according to the manufacturer's instructions.

3T3 cells were encapsulated in hydrogels generated from Alg-N (alginate-norbornene) and Alg-T (alginate-tetrazine) that had low versus high degrees of substitution at varying polymer concentrations (e.g., 1.5% or 3.0% w/v; i.e., 1.5 g alginate per 100 mL DMEM or 3 g alginate per 100 mL DMEM). Cells were stained with a commercial Live-Dead kit from Life Technologies. Degree of substitution is measured by nuclear magnetic resonance (NMR), comparing the integration of peaks of alginate protons to peaks of either alkene protons on norbornene, or tetrazine protons. A quantitative measure of degree of substitution can be obtained from this using the ratio of norbornene/tetrazine protons to the alginate protons to calculate a degree of substitution.

Figure 5A:
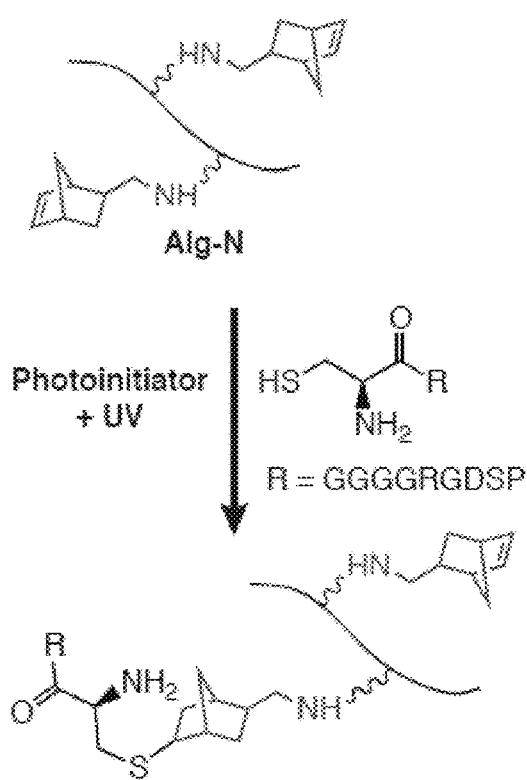
FIGS. 5A-E illustrate cell adhesion, spreading, and proliferation on click alginate hydrogels modified with RGD peptides after synthesis. Schematic of CGGGGRGDSP peptide coupling reaction onto click alginate hydrogel surface using photoinitiated thiol-ene chemistry (5A). Representative images of 3T3 fibroblast adhesion, spreading, and proliferation on click alginate hydrogels with varying RGD peptide density (scale bar=200 µm) (5B), and quantification (Two-Way ANOVA with Turkey's post-hoc test, *p<0.05, ****p<0.0001 relative to No RGD control; Values represent mean and standard deviation, n=4-7) by endogenous EGFP expression (green) over 3 days (7C). Phalloidin (red) and Hoescht 33342 (blue) staining of F-actin filaments and nuclei at 3 days for cells adherent to RGD modified click alginate hydrogels (scale bar=100 µm) (5D). Representative fluorescent images of EGFP (green) 3T3 cells cultured on click alginate hydrogels with varying ligand density for 3 days and stained with ethidium homodimer-1 (red) (scale bar=100 µm) (5E). The High, Low, and No RGD conditions refer to the 2 mM, 0.2 mM, and 0 mM peptide solutions used to modify the click alginate hydrogel surface.
Figure 5C:
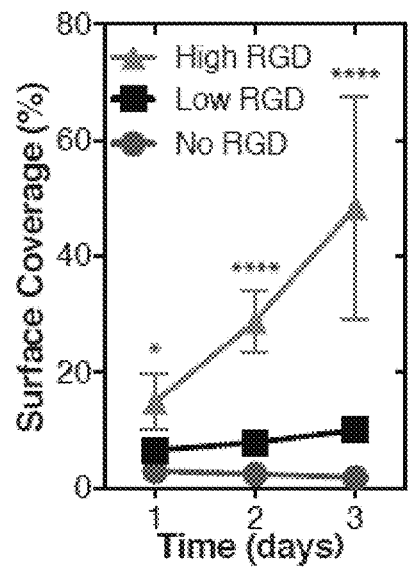
Figure 5D:
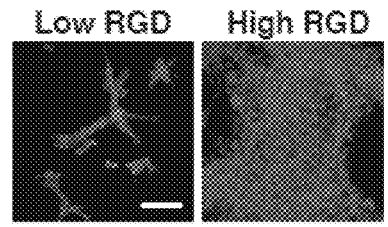
Figure 5B:
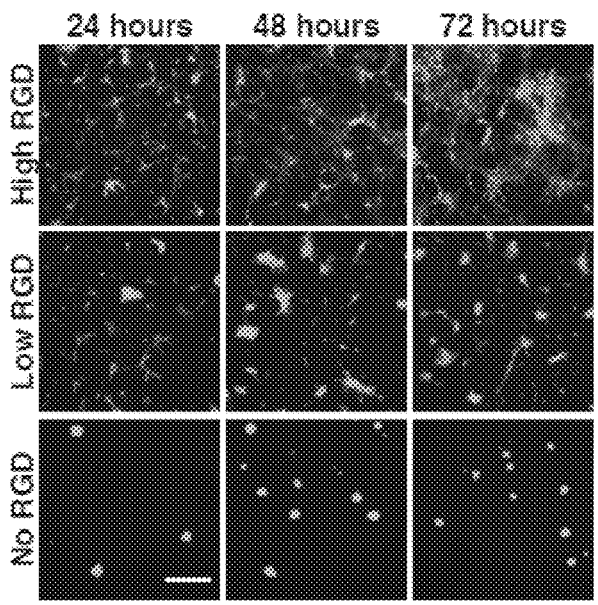

Cell viability and metabolic activity of cells encapsulated in click alginate hydrogels were also investigated over a 3 day culture period; ionically crosslinked hydrogels were used for comparison in these studies. Representative images of encapsulated cells stained with ethidium homodimer-1 show minimal cell death in both click and ionically crosslinked gels 4 hours and 3 days after encapsulation (FIG. 5A). Quantification revealed that click alginate hydrogels resulted in significantly higher viability of encapsulated 3T3 cells both immediately after encapsulation (93±1% vs. 87±2%) and after 3 days of culture (84±2% vs. 79±4%) (FIG. 5B). It should be noted that a loss in measured cell viability may occur during the cell retrieval process by enzymatic digestion of the hydrogels. The overall metabolic activity of the cells encapsulated in the different hydrogels was also analyzed, and noted to increase over the 3 day culture period for both hydrogel crosslinking chemistries (results not shown).

Example 5: Post-Gelation Thiol-Ene Photoreaction of Click-Crosslinked Hydrogels

Click alginate hydrogels were made as described above (2% w/v, N:T=2) and then a cell adhesive CGGGGRGDSP peptide (Peptide2.0) solution at 0.2 or 2 mM containing 0.5% w/v photoinitiator (Irgacure 2959; Sigma-Aldrich) was pipetted on top and the gel was covered with a glass coverslip. Gels were irradiated at 365 nm for 60 seconds at 10 mW/cm². The gels were washed several times with DMEM to remove excess photoinitiator and unreacted peptide and swollen to equilibrium at 37° C. before seeding with cells.

Figure 5E:
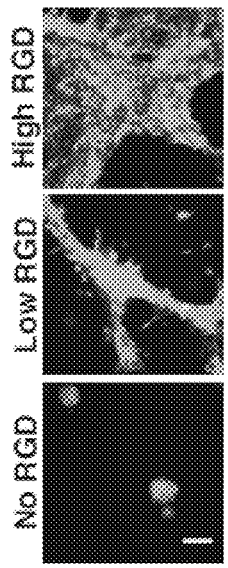

Thiol-containing molecules were grafted onto unreacted norbornenes in pre-formed click alginate hydrogels using a photoinitiated thiol-ene reaction (FIG. 5A). Gels with N:T=2 were used to ensure unreacted norbornenes were available to react after the initial gelation. RGD peptide solutions at high (2 mM) or low (0.2 mM) concentration were reacted onto the surface of these click alginate hydrogels and then gels were seeded with NIH 3T3 fibroblasts expressing a cytosolic fluorescent marker (EGFP). 3T3 cells readily adhered and spread on gels modified with RGD, while very few cells were able to attach or elongate on control gels with no RGD (FIG. 5B). Cells on click alginate hydrogels presenting RGD were able to form branched interconnected networks, with a significant RGD density-dependent 2-3 fold increase in surface coverage over the 3 day culture, while unmodified click alginate gels were observed to be non-cell-adhesive and showed a decrease in surface coverage by cells over time (FIG. 5C). After 3 days in culture, cells also showed an increase in spreading and actin stress fiber formation with higher RGD concentration (FIG. 5D). Additionally, the high viability of cells after 3 days of culture demonstrated the cytocompatibility of the click alginate hydrogels for 2D cell culture (FIG. 5E).

Example 6: In Vivo Hydrogel Inflammatory Response

Ultrapure alginate with low endotoxin levels (MVG alginate, ProNova Biomedical AS) was modified as described above with norbornene and tetrazine and subsequently prepared at 2% w/v in DMEM after purification. Click alginate hydrogels were prepared by mixing ultrapure Alg-N and Alg-T polymers with N:T=1 by connecting two syringes with a luer lock. 15 minutes after mixing, 50 µL of click alginate hydrogel was injected subcutaneously through an 18 G needle. For ionic hydrogel samples, a 2% w/v ultrapure alginate solution was prepared in DMEM and similarly mixed in a syringe with a CaSO$_4$ slurry at a final concentration of 2%. 50 µL of the ionically crosslinked gel was also injected subcutaneously in the same mice. Both gel samples were retrieved along with the surrounding skin after 1 week, 1 month, and 2 months of injection and fixed overnight in 10% neutral buffered formalin solution (Sigma-Aldrich). Samples were embedded in paraffin, sectioned, and stained with hematoxylin and eosin.

Figure 6A:
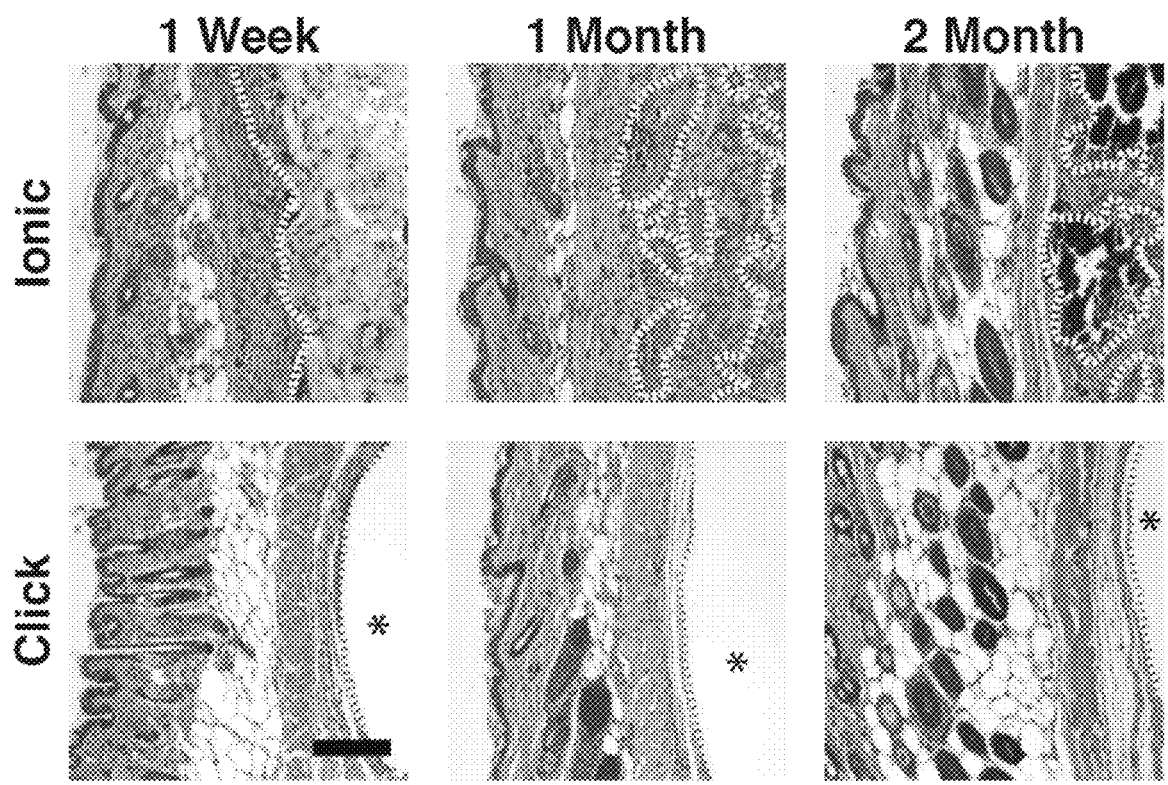
FIG. 6A illustrates tissue response following subcutaneous injection of click and ionically crosslinked hydrogels in vivo. Representative hematoxylin and eosin (H&E) stain of tissue sections at 1 week, 1 month, and 2 month following injection into BALB/cJ mice (scale bar=150 µm). Images focus on the gel-tissue interface, with dashed lines indicating the border between the hydrogel and the surrounding tissue. Asterisks indicate the location of the click alginate hydrogel, which separates from the tissue during histological analysis with no cell infiltration.
Figure 6B:
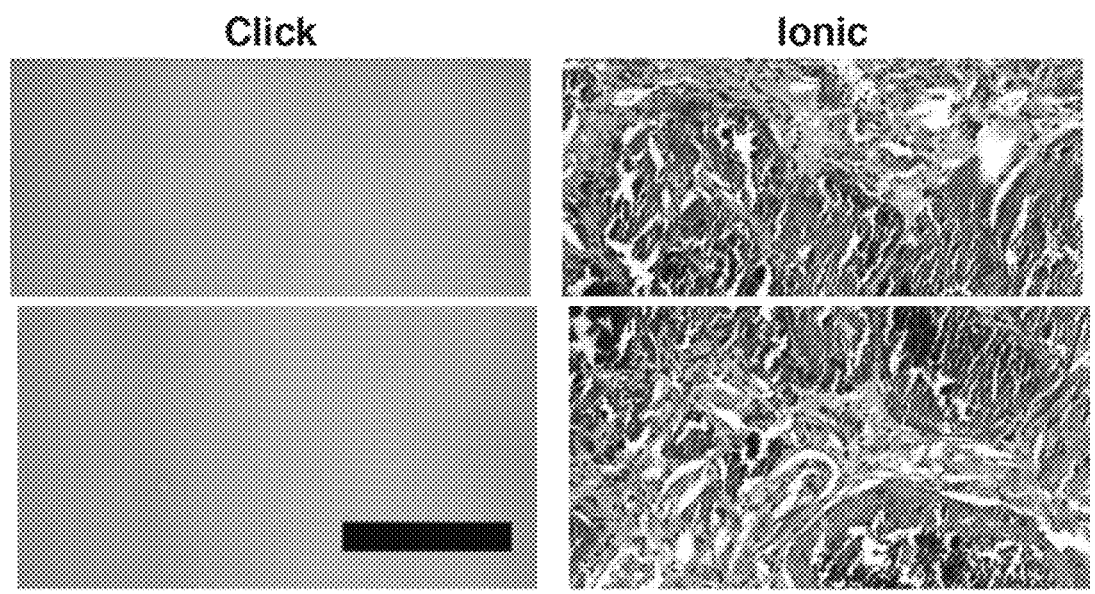
FIG. 6B focuses on interior of the hydrogel at 2 months following subcutaneous injection in vivo (scale bar=200 µm).

The inflammatory response to the injection of click alginate hydrogels in vivo was investigated next. Click crosslinked and ionically crosslinked alginate hydrogels were injected subcutaneously and retrieved after 1 week, 1 month, and 2 months. The gelation kinetics of click alginate hydrogels allows them to be mixed and readily injected, in a similar manner to ionically crosslinked hydrogels. A thin fibrous capsule was found to surround both types of gels 1 week after injection. H&E staining revealed a very thin capsule of collagen and fibroblasts surrounding the material throughout the duration of the study with minimal inflammation (FIG. 6A). At 1 month, the ionically crosslinked gels were seen to lose structural integrity and allowed for infiltration of fibroblasts and immune cells into the gel, while the click crosslinked samples showed no evidence of breakdown nor cell infiltration into the material for up to 2 months (see FIG. 6B), and maintained a thin layer of fibroblasts surrounding the gel.

Example 7: Preparation of Click Chitosan Hydrogels 4-(1,2,4,5-Tetrazin-3-yl)benzoic acid was synthesized according to previously published methods and purified by preparatory reverse-phase HPLC. 5-norbornene-2-carboxylic acid was purchased from Sigma Aldrich. Tetrazine (Tz) and Norbornene (Nb) acids are conjugated to Chitosan amines by solubilizing Tz or Nb in DMSO, adding EDC and NHS. Chitosan, solubilized overnight in 0.1 M HCl and then pH adjusted to ~6 through addition of 1M MES Buffer pH 6.5, is then added dropwise to the Tz/Nb DMSO solution. The reaction is allowed to react overnight at room temperature with stirring. The resulting solution is dialyzed against water and then lyophilized. The resulting materials are resuspended in physiologically relevant pH buffered solution or WFI are reacted to produce hydrogels.

Chitosan-Nb, Chitosan-Tz, and unmodified Chitosan polymers were dissolved in deuterium oxide (Sigma-Aldrich) at 1.5% w/v. 1H-NMR spectra were obtain on a 400 MHz NMR spectrometer (Varian). Degree of substitution is calculated by comparing the integral of the chitosan backbone proton peak δ 3.0 with either the alkene proton peaks of norbornene at δ 6.2-5.9 or with peak of tetrazine at δ 10.4 (s, 1H).

Example 8: Preparation of Click Gelatin Hydrogels

Figure 7A:
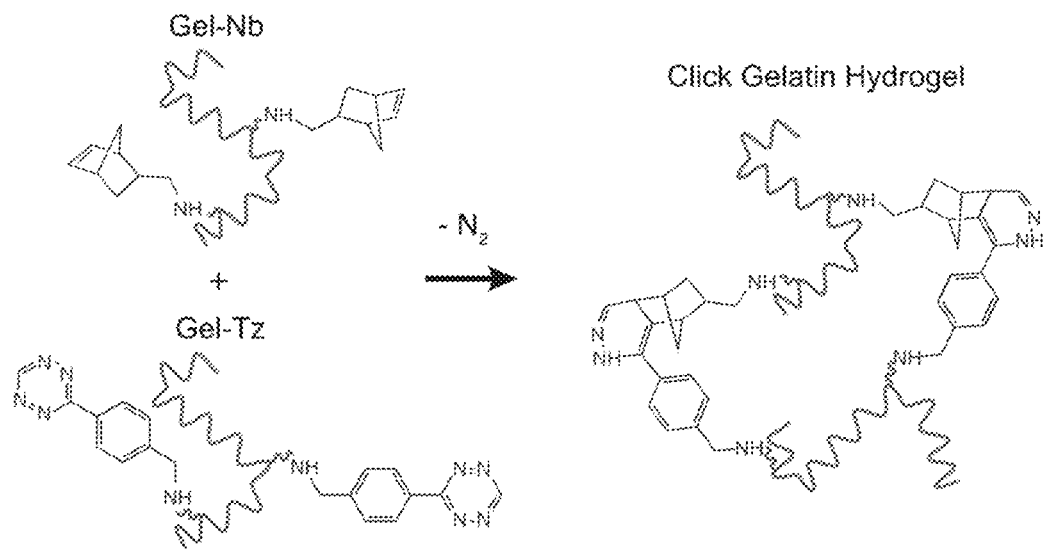
FIG. 7A is a schematic showing a click gelatin polymer cross-linking reaction where Gel-Tz and Gel-Nb polymers are mixed together to create a covalently crosslinked click alginate hydrogel network, with the loss of $N_2$.
Figure 7B:
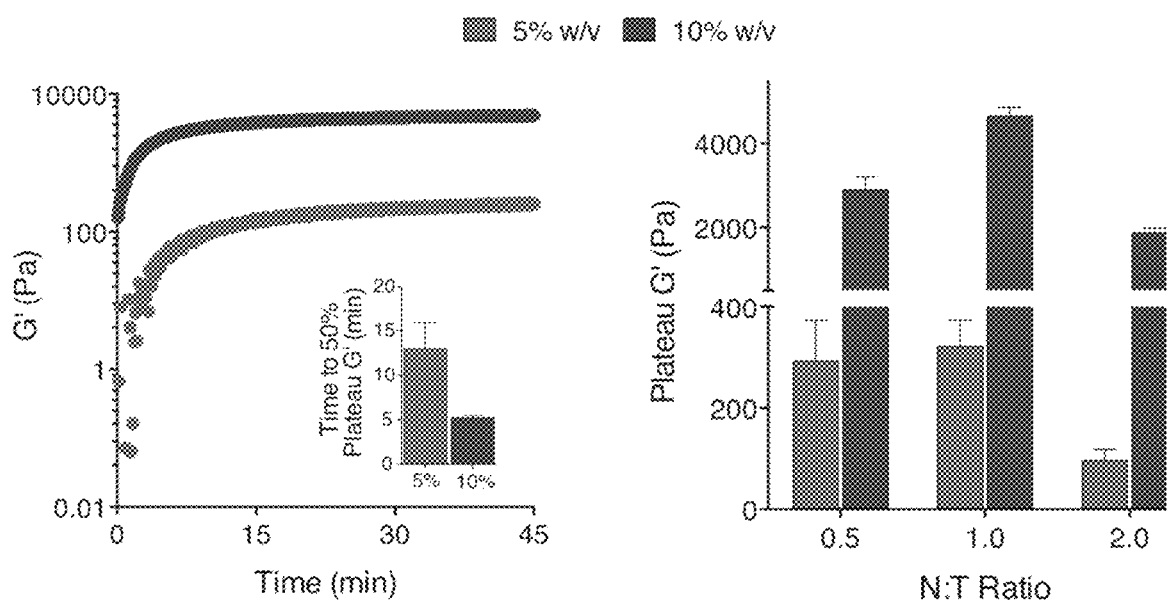
FIG. 7B (left) illustrates storage modulus (G') time sweeps (on rheometer) of click gelatin hydrogels at 37° C. at 5 and 10% w/v and N:T=1. Plateau modulus reached within 45 min for both, with inset showing time to 50% of plateau modulus. On the right, plateau storage modulus is shown as a function of N:T polymer ratio, wherein mechanical properties are controlled by changing the ratio of polymers that are being mixed (rather than amount of crosslinker or concentration of polymer).
Figure 8A:
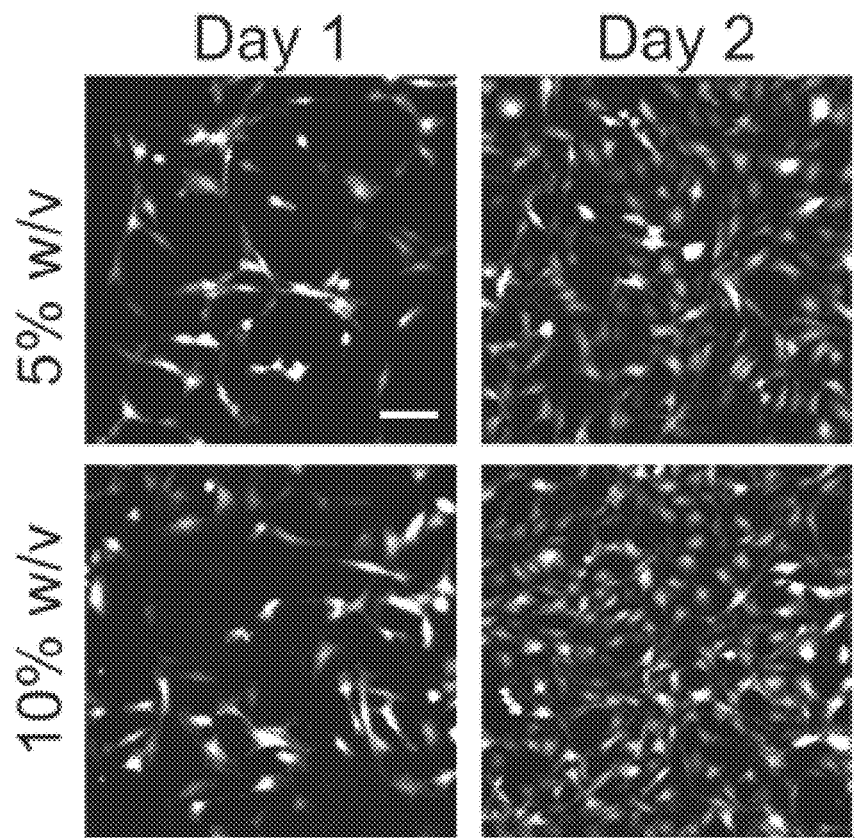
FIGS. 8A-B illustrate 3T3 fibroblast adhesion, spreading, and proliferation on click gelatin hydrogels.
Figure 8B:
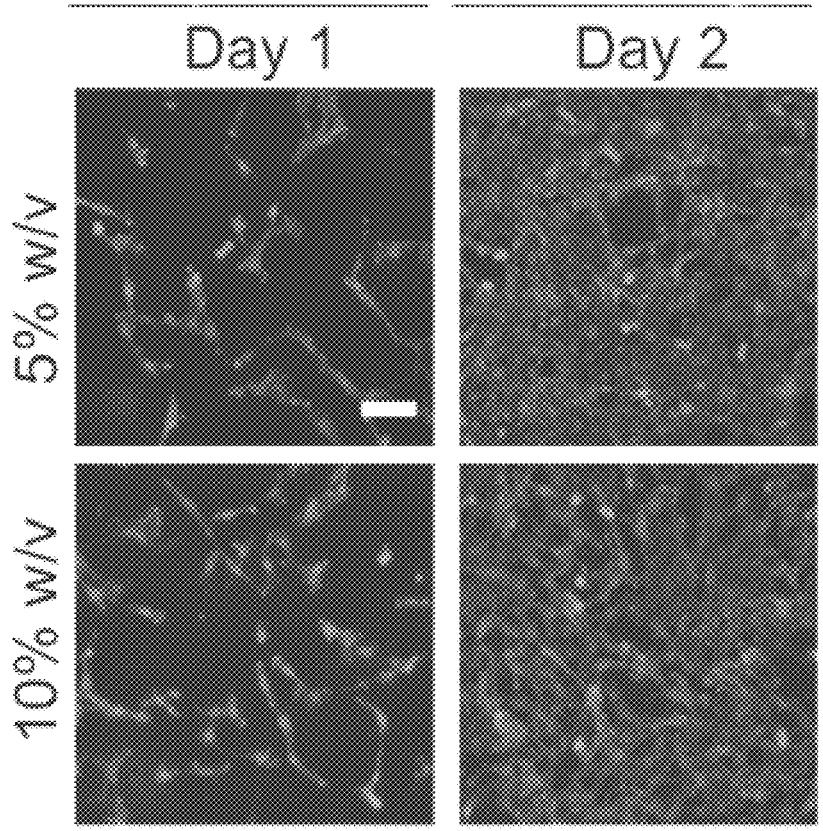

Similarly to alginate and chitosan hydrogels, gelatin was modified to prepare gelatin-tetrazine (Gel-Tz) and gelatin-norbornene (Gel-Nb). Gel-Tz and Gel-Nb polymers are mixed together to create a covalently crosslinked click gelatin hydrogel network, with the loss of $N_2$. (FIG. 7A). Storage modulus (G') time sweeps of click gelatin hydrogels at 5 and 10% w/v and N:T=1 show that plateau modulus were reached within 45 min for both materials, with inset showing time to 50% of plateau modulus. FIGS. 8A and 8B show 3T3 fibroblast adhesion, spreading, and proliferation on click gelatin hydrogels. Intrinsic cell adhesive peptide sequences of gelatin were preserved as cells were seen to readily adhere and spread very quickly on the surface of the gel (2D assay). F-actin and nuclei staining using Phalloidin and Hoescht of 3T3 fibroblast adhesion, spreading, and proliferation in FIG. 8B shows strong pull on the underlying matrix by the cells.

FIG. 9 shows that 3T3 fibroblasts retained high viability after 3D encapsulation in click crosslinked gelatin with an increase in metabolic activity over a three day culture period. Encapsulated 3T3 fibroblasts rapidly assumed a spread morphology within click crosslinked gelatin after one day (cell length: 80±6 μm), a phenotype that was inhibited in the presence of the broad-spectrum matrix metalloproteinase (MMP)-inhibitor marimastat (cell length: 16±2 μm), suggesting 3D cell spreading in click crosslinked gelatin was dependent on MMP-mediated degradation of the gelatin matrix While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this disclosure has been particularly shown and described with references to preferred embodiments thereof, it will be understood by those skilled in the art that various changes in form and details may be made therein without departing from the scope of the disclosure encompassed by the appended claims.

We claim:

1. A hydrogel comprising a first polymer and a second polymer, wherein the first polymer and the second polymer are the same polymer and are both gelatin, wherein the first polymer is connected to the second polymer by linkers of formula (A):

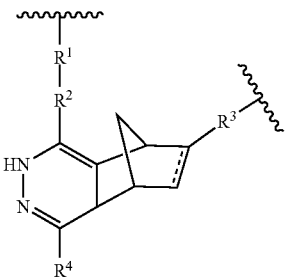

(A)

wherein
bond ═══ is a single or a double bond;
$R^1$ is —$C_0$-$C_6$ alkyl-NH—, —$C_0$-$C_6$ alkyl-O—, or —$C_0$-$C_3$alkyl-C(O)—;
$R^2$ is a bond, aryl, or heteroaryl, wherein aryl and heteroaryl are optionally substituted with halogen, hydroxy, $C_1$-$C_6$ alkyl, $C_1$-$C_6$ alkoxy, ($C_1$-$C_6$ alkyl)amino, or di($C_1$-$C_6$ alkyl)amino;
$R^3$ is —$C_0$-$C_6$ alkyl-NH—, —$C_0$-$C_6$ alkyl-O—, or —$C_0$-$C_3$alkyl-C(O)—; and
$R^4$ is hydrogen, $C_1$-$C_6$ alkyl, aryl, or heteroaryl, wherein aryl and heteroaryl are optionally substituted with halogen, hydroxy, $C_1$-$C_6$ alkyl, $C_1$-$C_6$ alkoxy, ($C_1$-$C_6$ alkyl)amino, or di($C_1$-$C_6$ alkyl)amino;
wherein the hydrogel is capable of being generated in the presence of a cell or a biological factor without damaging the cell or the biological factor.

2. The hydrogel according to claim 1, wherein:
bond ═══ is a single bond;
$R^1$ is —$C_0$-$C_6$ alkyl-NH—, or —$C_0$-$C_3$alkyl-C(O)—;
$R^2$ is a bond or aryl optionally substituted with halogen, hydroxy, $C_1$-$C_6$ alkyl, $C_1$-$C_6$ alkoxy, ($C_1$-$C_6$ alkyl) amino, or di($C_1$-$C_6$ alkyl)amino;
$R^3$ is —$C_0$-$C_6$ alkyl-NH—, or —$C_0$-$C_3$alkyl-C(O)—; and
$R^4$ is hydrogen, $C_1$-$C_6$ alkyl, or heteroaryl, wherein heteroaryl is optionally substituted with halogen, hydroxy, $C_1$-$C_6$ alkyl, $C_1$-$C_6$ alkoxy, ($C_1$-$C_6$ alkyl)amino, or di($C_1$-$C_6$ alkyl)amino.

3. The hydrogel according to claim 2, wherein $R^1$ and $R^3$ are both -methyl-NH—; or $R^1$ and $R^3$ are both —C(O)—.

4. The hydrogel according to claim 1, wherein the linkers of formula (A) are selected from the group consisting of formula (I):

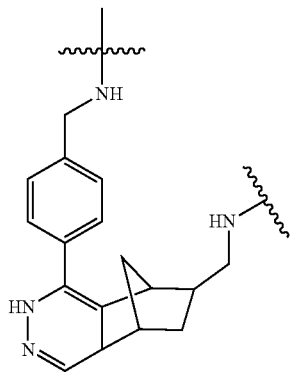

(I)

or formula (II):

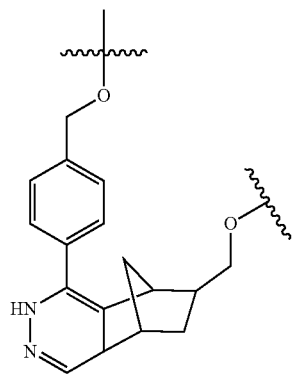

(II)

or formula (III):

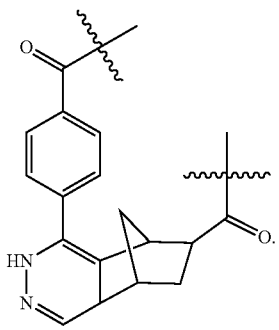

(III)

5. The hydrogel of claim 1, wherein the first polymer or the second polymer further comprises a cell adhesive peptide.

6. The hydrogel of claim 5, wherein the cell adhesive peptide comprises the amino acid sequence arginine-glycine-aspartic acid (RGD).

7. The hydrogel of claim 6, wherein the cell adhesive peptide comprises the amino acid sequence arginine-glycine-aspartic acid-cysteine (RGDC) (SEQ ID NO: 1).

8. The hydrogel of claim 1, wherein the Young's modulus of the hydrogel is 50 to 50,000 Pa.

9. The hydrogel of claim 1, wherein the hydrogel further comprises a cell, a biological factor, and/or a small molecule.

10. The hydrogel of claim 9, wherein the cell is a mammalian cell.

11. The hydrogel of claim 9, wherein the biological factor is a protein, nucleic acid, lipid, or carbohydrate.

12. The hydrogel of claim 11, wherein the protein is a growth factor or fragment thereof or an antibody or fragment thereof.

13. A method for preparing a hydrogel of claim 1, comprising,
a) providing a first polymer comprising a tetrazine moiety and a second polymer comprising a norbornene moiety wherein the first polymer and the second polymer are the same polymer and are both gelatin;
b) contacting the second polymer with the first polymer to form the hydrogel of claim 1.

14. The method of claim 13, wherein: (i) each molecule of the first polymer comprises 1-50,000 tetrazine moieties; (ii) each molecule of the second polymer comprises 1-50,000 norbornene moieties; and/or (iii) step b) comprises contacting a second polymer with a first polymer at a ratio of about 1:10 to about 10:1.

15. The method of claim 13, further comprising reacting the first polymer with a) benzyl amine tetrazine, benzyl alcohol tetrazine, or benzoic acid tetrazine, and a b) coupling agent to provide the first polymer comprising a tetrazine moiety.

16. The method of claim 15, wherein the coupling agent is 1-ethyl-3-(3-dimethylaminopropyl)carbodiimide (EDC).

17. The method of claim 13, further comprising reacting the second polymer with a) norbornene methanamine, norbornene methanol, or norbornene carboxylic acid, and b) a coupling agent to provide the second polymer comprising a norbornene moiety.

18. The method of claim 17, wherein the coupling agent comprises 1-ethyl-3-(3-dimethylaminopropyl)carbodiimide (EDC) and optionally N-Hydroxysuccinimide (NHS).

19. A method of regenerating a tissue in a subject in need thereof, the method comprising contacting the tissue with the hydrogel of claim 1.

20. A method of delivering a cell, a biological factor and/or a small molecule to a subject, the method comprising administering to the subject the hydrogel of claim 9, wherein after administration of the hydrogel, the cell, the biological factor and/or the small molecule is released from the hydrogel into a surrounding tissue of the subject, thereby delivering the cell, the biological factor and/or the small molecule to the subject.

* * * * *